US009095567B2

(12) United States Patent
Khandke et al.

(10) Patent No.: US 9,095,567 B2
(45) Date of Patent: Aug. 4, 2015

(54) VACCINE FORMULATIONS

(75) Inventors: Lakshmi Khandke, Nanuet, NY (US); Abbas Rashidbaigi, Basking Ridge, NJ (US)

(73) Assignee: Wyeth LLC, New York, NY (US)

( * ) Notice: Subject to any disclaimer, the term of this patent is extended or adjusted under 35 U.S.C. 154(b) by 221 days.

(21) Appl. No.: 13/701,707

(22) PCT Filed: May 25, 2011

(86) PCT No.: PCT/IB2011/052275

§ 371 (c)(1), (2), (4) Date: Dec. 3, 2012

(87) PCT Pub. No.: WO2011/151760

PCT Pub. Date: Dec. 8, 2011

(65) Prior Publication Data

US 2013/0072881 A1 Mar. 21, 2013

Related U.S. Application Data

(60) Provisional application No. 61/351,804, filed on Jun. 4, 2010.

(51) Int. Cl.

| | |
|---|---|
| ***A61K 39/385*** | (2006.01) |
| ***A61K 39/09*** | (2006.01) |
| ***A61K 39/095*** | (2006.01) |
| ***A61K 39/00*** | (2006.01) |
| ***A61K 47/48*** | (2006.01) |
| ***A61M 5/24*** | (2006.01) |
| ***A61M 5/31*** | (2006.01) |

(52) U.S. Cl.

CPC ............. *A61K 39/385* (2013.01); *A61K 39/092* (2013.01); *A61M 5/24* (2013.01); *A61M 5/3129* (2013.01)

(58) Field of Classification Search

None

See application file for complete search history.

(56) References Cited

U.S. PATENT DOCUMENTS

| | | | | |
|---|---|---|---|---|
| 4,673,574 | A | 6/1987 | Anderson | |
| 4,902,506 | A | 2/1990 | Anderson et al. | |
| 4,912,094 | A | 3/1990 | Myers et al. | |
| 5,057,540 | A | 10/1991 | Kensil et al. | |
| 5,078,996 | A | 1/1992 | Conlon et al. | |
| 5,118,794 | A | 6/1992 | Grangeorge et al. | |
| 5,163,918 | A | 11/1992 | Righi et al. | |
| 5,254,339 | A | 10/1993 | Morein | |
| 5,614,382 | A | 3/1997 | Metcalf | |
| 5,723,127 | A | 3/1998 | Scott et al. | |
| 6,113,918 | A | 9/2000 | Johnson et al. | |
| 6,207,646 | B1 | 3/2001 | Krieg et al. | |
| 6,224,880 | B1 | 5/2001 | Chan et al. | |
| 6,270,775 | B1 | 8/2001 | Cleary | |
| 6,355,255 | B1 | 3/2002 | Cleary et al. | |
| 6,951,653 | B2 | 10/2005 | Cleary et al. | |
| 7,935,787 | B2 * | 5/2011 | Khandke et al. | 530/350 |
| 8,361,477 | B2 * | 1/2013 | Borkowski | 424/184.1 |
| 8,444,992 | B2 * | 5/2013 | Borkowski | 424/184.1 |
| 8,562,999 | B2 * | 10/2013 | Khandke et al. | 424/184.1 |
| 8,603,484 | B2 * | 12/2013 | Prasad | 424/184.1 |
| 8,678,184 | B2 * | 3/2014 | Kraus et al. | 206/223 |
| 8,784,826 | B2 * | 7/2014 | Borkowski | 424/184.1 |
| 8,808,707 | B1 * | 8/2014 | Siber et al. | 424/197.11 |
| 8,808,708 | B2 * | 8/2014 | Hausdorff et al. | 424/197.11 |
| 8,895,024 | B2 * | 11/2014 | Hausdorff et al. | 424/197.11 |
| 8,895,329 | B2 * | 11/2014 | Yoon et al. | 438/22 |
| 8,895,724 | B2 * | 11/2014 | Hausdorff et al. | 536/124 |
| 2004/0047882 | A1 | 3/2004 | Broeker | |
| 2006/0210557 | A1 | 9/2006 | Luisi et al. | |
| 2006/0228380 | A1 | 10/2006 | Hausdorff et al. | |
| 2008/0069835 | A1 | 3/2008 | Boutriau et al. | |
| 2011/0201791 | A1 * | 8/2011 | Prasad | 530/403 |
| 2012/0237542 | A1 * | 9/2012 | Hausdorff et al. | 424/197.11 |
| 2013/0034580 | A1 * | 2/2013 | Khandke et al. | 424/197.11 |
| 2013/0072881 | A1 * | 3/2013 | Khandke et al. | 604/191 |
| 2013/0209510 | A1 * | 8/2013 | Hora | 424/209.1 |
| 2013/0259896 | A1 * | 10/2013 | Khandke et al. | 424/197.11 |
| 2013/0273098 | A1 * | 10/2013 | Blue et al. | 424/197.11 |
| 2014/0044748 | A1 * | 2/2014 | Lee | 424/194.1 |
| 2014/0081005 | A1 * | 3/2014 | Gerber et al. | 530/391.9 |

(Continued)

FOREIGN PATENT DOCUMENTS

| | | | |
|---|---|---|---|
| EP | 0941738 | A1 | 9/1999 |
| EP | 1296713 | B1 | 9/2003 |

(Continued)

OTHER PUBLICATIONS

Geier et al, MEd. Sci. Monit., 2010, 16(5):SR21-27.*

Offit et al, Pediatrics, 2003, 112:1394-1401.*

Lowe, I., et al., "The antimicrobial activity of phenoxyethanol in vaccines", Letters in Applied Microbiology, 18 (2):115-116 (1994).

Baldwin, R.N., "Contamination of Insulin by Silicone Oil: a Potential Hazard of Plastic Insulin Syringes", Diabetic Medicine, 5:789-790 (1988).

Bartzoka, V., et al., "Protein-Silicone Interactions: How Compatible Are the Two Species?", Langmuir, 14 (7):1887-1891 (1998).

Bartzoka, V., et al., "Silicone-Protein Films: Establishing the Strength of the Protein-Silicone Interaction", Langmuir, 14(7):1892-1898 (1998).

Bartzoka, V., et al., "Protein-Silicone Synergism at Liquid/Liquid Interfaces", Langmuir, 16(10):4589-4593 (2000).

(Continued)

*Primary Examiner* — Nita M Minnifield

(74) *Attorney, Agent, or Firm* — Victoria S. Molenda

(57) ABSTRACT

An immunogenic composition comprising a plurality of capsular polysaccharides from *Streptococcus pneumoniae* serotypes 1, 3, 4, 5, 6A, 6B, 7F, 9V, 14, 18C, 19A, 19F and 23F conjugated to a carrier protein, and further comprising at least one preservative, preferably 2-phenoxyethanol (2-PE). The preservative-containing immunogenic compositions of the invention confer resistance to one or more micro-organisms and are useful for producing multi-dose vaccine formulations having advantageous properties with respect to long term stability of the different antigenic determinants in the immunogenic composition of choice. Related compositions and methods for measuring the efficacy of one or more preservatives in a vaccine formulation are also provided.

24 Claims, 15 Drawing Sheets

(56) References Cited

U.S. PATENT DOCUMENTS

| | | | | |
|---|---|---|---|---|
| 2014/0314805 | A1* | 10/2014 | Hausdorff et al. | 424/197.11 |
| 2015/0056250 | A1* | 2/2015 | Kapre | 424/217.1 |

FOREIGN PATENT DOCUMENTS

| | | | |
|---|---|---|---|
| EP | 1326634 | B1 | 4/2006 |
| JP | 7236483 | A | 9/1995 |
| JP | 10201844 | A | 8/1998 |
| RU | 37462 | U1 | 4/2004 |
| UA | 67144 | A | 6/2004 |
| WO | 90/14837 | A1 | 12/1990 |
| WO | 92/19265 | A1 | 11/1992 |
| WO | 93/13202 | A1 | 7/1993 |
| WO | 94/00153 | A1 | 1/1994 |
| WO | 95/17210 | A1 | 6/1995 |
| WO | 96/33739 | A1 | 10/1996 |
| WO | 97/26008 | A1 | 7/1997 |
| WO | 98/13052 | A1 | 4/1998 |
| WO | 00/18434 | A1 | 4/2000 |
| WO | 00/56360 | A2 | 9/2000 |
| WO | 00/62801 | A2 | 10/2000 |
| WO | 01/41800 | A2 | 6/2001 |
| WO | 02/05846 | A1 | 1/2002 |
| WO | 02/098368 | A2 | 12/2002 |
| WO | 02/098369 | A2 | 12/2002 |
| WO | 03/039485 | A2 | 5/2003 |
| WO | 03/063766 | A2 | 8/2003 |
| WO | 2004/065603 | A2 | 8/2004 |
| WO | 2004/067030 | A2 | 8/2004 |
| WO | 2004/071439 | A2 | 8/2004 |
| WO | 2004/083251 | A2 | 9/2004 |
| WO | 2004/094596 | A2 | 11/2004 |
| WO | 2005/000244 | A2 | 1/2005 |
| WO | 2005/039620 | A1 | 5/2005 |
| WO | 2006/110381 | A1 | 10/2006 |
| WO | 2007/026249 | A2 | 3/2007 |
| WO | 2007/127668 | A2 | 11/2007 |
| WO | 2008/079653 | A1 | 7/2008 |
| WO | 2008/079732 | A2 | 7/2008 |
| WO | 2008/143709 | A2 | 11/2008 |
| WO | 2009/109550 | A1 | 9/2009 |

OTHER PUBLICATIONS

Bartzoka, V., et al., "Chapter 21: Protein-Silicone Interactions at Liquid-Liquid Interfaces", Emulsions, Foams and Thin Films, Dekker, New York, Mittal & Kumar (eds.), pp. 371-380 (2000).
Bernstein, R.K., "Clouding and Deactivation of Clear (Regular) Human Insulin: Association With Silicone Oil From Disposable Syringes?", Diabetes Care, 10(6):786-787 (1987).
Bolgiano, B., et al., "Effect of physico-chemical modification on the immunogenicity of Haemophilus influenzae type b oligosaccharide-CRM197 conjugate vaccines", Vaccine, 19:3189-3200 (2001).
Chantelau, E.A., et al., "Pollution of Insulin With Silicone Oil, a Hazard of Disposable Plastic Syringes", The Lancet, 1:1459 (1985).
Chantelau, E., et al., "Silicone Oil Released From Disposable Insulin Syringes", Diabetes Care, 9(6):672-673 (1986).
Chantelau, E., "Silicone oil contamination of insulin", Diabetic Medicine, 6:278 (1989).
Chen, C-C, et al., "Immunogenicity and Reactogenicity of Two Recombinant Hepatitis B Vaccines in Healthy Adolescents on Two-dose Schedule", Acta Pediatrica Sinica, 40(3):157-160 (1999).
Collier, F.C., et al., "Insulin Syringes and Silicone Oil", The Lancet, 326:611 (1985).
Dawson, et al., Handbook of Biochemist, pp. 352-353; 238-239; 357-358 (1991).
Gunn, K.E., et al., "A role for the unfolded protein response in optimizing antibody secretion", Molecular Immunology, 41:919-927 (2004).
Ho, M.M., et al., "Solution stability studies of the subunit components of meningococcal C oligosaccharide-CRM197 conjugate vaccines", Biotechnol. Appl. Biochem., 33:91-98 (2001).
Ho, M.M, et al., "Physico-chemical and immunological examination of the thermal stability of tetanus toxoid conjugate vaccines", Vaccine, 20:3509-3522 (2002).
Jones, L.S., et al., "Silicone Oil Induced Aggregation of Proteins", Journal of Pharmaceutical Sciences, 94(4):918-927 (2005).
Kajihara, M., et al., "Development of new drug delivery system for protein drugs using silicone (I)", Journal of Controlled Release, 66:49-61 (2000).
Khandke, L., et al., "Preservative of choice for Prev(e)nar 13TM in a multi-dose formulation", Vaccine, 29 (41):7144-7153 (2011).
Meyer, B.K., et al., "Antimicrobial Preservative Use in Parenteral Products: Past and Present", Journal of Pharmaceutical Sciences, 96(12):3155-3167 (2007).
PCT International Search Report for PCT/US2007/066959 mailed Jul. 28, 2008.
Polin, J.B., "The Ins and Outs of Prefilled Syringes", Pharmaceutical and Medical Packaging News, available at http://www.pmpnews.com/article/ins-and-outs-prefilled-syringes, 7 pages (2003).
Sun, L., et al., "Protein denaturation induced by cyclic silicone", Biomaterials, 18:1593-1597 (1997).
Yoshida, H., et al., "XBP1 mRNA Is Induced by ATF6 and Spliced by IRE1 in Response to ER Stress to Produce a Highly Active Transcription Factor", Cell, 107(7):881-891 (2001).
Drain, P.K., et al., "Single-dose versus multi-dose vaccine vials for immunization programmes in developing countries", Bull World Health Organ, 81(10):726-731 (2003).
Fernsten, P., et al., "13-valent pneumococcal conjugate vaccine immune sera protects against pneumococcal serotype 1, 3, and 5 bacteremia in a neonatal rat challenge model", Hum Vaccin, 7:Suppl 75-84 (2011).
Paoletti, L.C., "Potency of clinical group B streptococcal conjugate vaccines", Vaccine, 19:2118 (2001).
Sharma, B., et al., "A simple and rapid method for quantifying 2-phenoxyethanol (2-PE) in Diphtheria, Tetanus and w-Pertussis (DTwP) vaccine", Biologicals, 36(1):61-63 (2008).
Wilson, G.S., Chapter 7: "Faulty Production: Bacterial Contamination of Vaccine or Antiserum", The Hazards of Immunization, The Athlone Press, London, pp. 75-78 (1967).
Bryant, K.A., et al., "Safety and Immunogenicity of a 13-Valent Pneumococcal Conjugate Vaccine", Pediatrics, 125:866-875 (2010).

* cited by examiner

Figure 1

Thimerosal Effectiveness in Various Formulations

| Formulation | Thimerosal Hg Con., µg/dose (%) | Measured Hg Con. µg/dose | Multi Challenge[$] | Single-Challenge | Multi Challenge[$] | Single-Challenge |
|---|---|---|---|---|---|---|
| | | | EP (A) | EP (A) | EP (B) | EP (B) |
| Prev(e)nar 13™ | 100µg (0.04) | ND | ND | Fail | ND | **Pass** |
| Prev(e)nar 13™ | 50µg (0.02) | 41.4 ± 2.9 | Fail | Fail | Fail | **Pass** |
| Prev(e)nar 13™ | 25µg (0.01) | 22.0 ± 3.6 | Fail | Fail | Fail | Fail |
| Saline Control | 50µg (0.02) | 43.2 ± 3.7 | Fail | Fail | Fail | **Pass** |

ND stands for not determined

The actual mercury concentration measured by CVAAS are the mean ± Standard Deviation in triplicates

[$] For multi-challenge studies, only anti-bacterial effectiveness method outlined in EP and not the anti-yeast or anti-mold criteria was evaluated.

Figure 2

2-PE effectiveness and stability in vaccine formulation at various concentrations

| Formulation | 2-PE Con., mg/dose | Measured 2-PE Con., mg/dose | Storage Time/Condition | Single-Challenge EP (A) | Single-Challenge EP (B) |
|---|---|---|---|---|---|
| Prev(e)nar 13 | 0 | ND | 0 | Fail | Fail |
| Prev(e)nar 13 | 0 | ND | 1 month 37°C | Fail | Fail |
| Prev(e)nar 13 | 0 | ND | 2.5 Years 2-8°C | Fail | Fail |
| Prev(e)nar 13 | 2.5 | ND | 0 | Fail | Fail |
| Prev(e)nar 13 | 2.5 | ND | 1 month 37°C | Fail | Fail |
| Prev(e)nar 13 | 3.5 | 3.4 | 0 | Fail | Pass |
| Prev(e)nar 13 | 3.5 | 3.3 | 1 month 37°C | Fail | Pass |
| Prev(e)nar 13 | 3.5 | 3.5 | 2.5 Years 2-8°C | Fail | Pass |
| Prev(e)nar 13 | 4.5 | ND | 0 | Fail | Pass |
| Prev(e)nar 13 | 4.5 | ND | 1 month 37°C | Fail | Pass |
| Prev(e)nar 13 | 5.0 | 4.8 | 0 | Fail | Pass |
| Prev(e)nar 13 | 5.0 | 4.8 | 1 month 37°C | Fail | Pass |
| Prev(e)nar 13 | 5.0 | 5.2 | 2.5 Years 2-8°C | Fail | Pass |
| Prev(e)nar 13 | 5.5 | ND | 0 | Fail | Pass |
| Prev(e)nar 13 | 5.5 | ND | 1 month 37°C | Pass | Pass |
| Prev(e)nar 13 | 6.0 | ND | 0 | Pass | Pass |
| Prev(e)nar 13 | 6.0 | ND | 1 month 37°C | Pass | Pass |
| Prev(e)nar 13 | 6.5 | ND | 0 | Pass | Pass |
| Prev(e)nar 13 | 6.5 | ND | 1 month 37°C | Pass | Pass |
| Prev(e)nar 13 | 7.0 | ND | 0 | Pass | Pass |
| Prev(e)nar 13 | 7.0 | ND | 1 month 37°C | Pass | Pass |
| Prev(e)nar 13 | 7.5 | 7.3 | 0 | Pass | Pass |
| Prev(e)nar 13 | 7.5 | 7.2 | 1 month 37°C | Pass | Pass |
| Prev(e)nar 13 | 7.5 | 7.6 | 2.5 Years 2-8°C | Pass | Pass |
| Prev(e)nar 13 | 8.0 | ND | 0 | ND | Pass |
| Prev(e)nar 13 | 10.0 | ND | 0 | ND | Pass |

ND stands for not determined

The actual 2-PE concentration was measured by RP-HPLC

SA=Staphylococcus aureus ; PA=Pseudomonas aeruginosa; CA=Candida albicans; AN=Aspergillus niger SA=Staphylococcus aureus ; PA=Pseudomonas aeruginosa; CA=Candida albicans; AN=Aspergillus niger Single challenge – vaccine formulation with 5 mg/0.5 mL 2-phenoxyethanol at 20-25°C SA=Staphylococcus aureus ; PA=Pseudomonas aeruginosa; CA=Candida albicans; AN=Aspergillus niger SA=Staphylococcus aureus ; EC=*E. coli* ; PA=Pseudomonas aeruginosa; BS=*B. subtilis*

SA=Staphylococcus aureus ; EC=*E. coli* ; PA=Pseudomonas aeruginosa; BS=*B. subtilis*

SA=Staphylococcus aureus ; EC=*E. coli* ; PA=Pseudomonas aeruginosa; BS=*B. subtilis*

SA=Staphylococcus aureus ; EC=*E. coli* ; PA=Pseudomonas aeruginosa; BS=*B. subtilis*

Figure 12

**Nonlinear Regression Analysis of *S. aureus* Decay in Various Challenge Studies**

| Formulation | Method | Temp After Challenge (°C) | 50% Decay (Days) | Slope ($log_{10}$ Decay/Day) | $R^2$ |
|---|---|---|---|---|---|
| vaccine + 5 mg/dose 2-PE | Single | 20 – 25 | 0.45 | -0.15 | 0.99 |
| vaccine + 0.01% Thimerosal | Single | 20 – 25 | 2.11 | -0.72 | 0.99 |
| saline + 0.02% Thimerosal | Single | 20 – 25 | 0.84 | -0.31 | 1.00 |
| vaccine + 0.02% Thimerosal | Single | 20 – 25 | 1.86 | -0.64 | 0.99 |
| vaccine + 5 mg/dose 2-PE | Multiple | 22 – 24 | 0.14 | -0.13 | 0.98 |
| vaccine + 0.01% Thimerosal | Multiple | 22 – 24 | 6.20 | -1.39 | 0.99 |
| saline + 0.02% Thimerosal | Multiple | 22 – 24 | 3.28 | -1.41 | 0.99 |
| vaccine + 0.02% Thimerosal | Multiple | 22 – 24 | 6.97 | -1.82 | 0.99 |
| vaccine + 5 mg/dose 2-PE | Multiple | 2 – 8 | 0.03 | -0.07 | 0.96 |
| vaccine + 0.01% Thimerosal | Multiple | 2 – 8 | 30.28 | -5.98 | 0.99 |
| saline + 0.02% Thimerosal | Multiple | 2 – 8 | 9.13 | -1.47 | 0.99 |
| vaccine + 0.02% Thimerosal | Multiple | 2 – 8 | 19.24 | -5.27 | 0.99 |

Figure 13

| Preservative | 0.5mL Dose Target | Multi-challenge Criteria EP-B* | Single challenge Criteria EP-B* |
|---|---|---|---|
| None | 0 | Fail | Fail |
| Thimerosal reference | 50μg Hg | Fail | Pass |
| Thimerosal reference | 25μg Hg | Fail | Fail |
| Saline Control | 50μg Hg | Fail | Pass |
| 2-PE | 5.0mg | Pass | Pass |

* EP criteria 5.1.3 Criteria "B"

Long term stability of Prev(e)nar 13 containing 2-PE

Long term stability of 2-PE

2-PE in a Prev(e)nar 13 formulation is stable for 2.5 years at 2-8°C

VACCINE FORMULATIONS

CROSS REFERENCE TO RELATED APPLICATIONS

This application is the national phase of Int'l Appl. No. PCT/IB2011/052275, filed May 25, 2011, which claims the priority benefit of U.S. Provisional Appl. No. 61/351,804, filed Jun. 4, 2010, the entirety of which are hereby incorporated by reference.

BACKGROUND OF THE INVENTION

Pneumococcal disease caused by the bacterium *Streptococcus pneumoniae* (also known as pneumococcus) is one of the more important bacterial pathogens across globe. The disease burden is high in the developing countries in children under five years of age where the vaccine is not available. Pneumococcal disease is a complex group of illnesses and includes invasive infections such as bacteremia/sepsis, meningitis, pneumonia and otitis media, which affects both children and adults. Prevnar 13 (also known as "Prevenar 13" and referred to herein as "Prev(e)nar 13") is a formulation of polysaccharides from thirteen pneumococcal serotypes (1, 3, 4, 5, 6A, 6B, 7F, 9V, 14, 18C, 19A, 19F and 23F)) which are individually conjugated to $CRM_{197}$ (Cross Reactive Material from a mutant strain of *Corynebacterim diphtheriae*). Prev(e)nar 13 is recommended for active immunization of infants and toddlers to provide the broadest serotype coverage of any pneumococcal conjugate vaccines. Notably, serotype 19A in Prev(e)nar 13 is prevalent in many regions of the world and is often associated with antibiotic resistance. See e.g., WO2006/110381; WO2008/079653; WO2008/079732; WO2008/143709 and references cited therein.

Thimerosal (also known as Thiomersal; merthiolate) is an ethylmercury-containing preservative which has, since the early 1930s, been added to many multi-dose injectable formulations and topical solutions to protect them from potential contamination during exposure and when administered to multiple subjects. Thimerosal continues to be administered, as part of mandated immunizations and in other pharmaceutical products in the United States and the rest of the world. It is claimed to be an effective preservative for eliminating potential contaminating bacteria during multiple use of products in the field, with minimum interaction with the antigenic structure and properties of vaccines. Due to mounting controversies regarding potential safety issues and adverse effects of ethylmercury on brain development in infants and youth, certain agencies began recommending that alternative preservatives with a lower or negligible safety risk be identified. In 1999, a U.S. Food and Drug Administration review mandated by the U.S. Congress found that some infants might receive more mercury from vaccines than was considered acceptable according to certain national guidelines. The American Academy of Pediatrics (AAP) and US Public Health Service (USPHS) issued a joint statement concerning Thimerosal in vaccines and then the AAP released an interim report to clinicians recommending removal of Thimerosal from vaccines as soon as possible, while maintaining efforts to ensure high levels of vaccination continue to be implemented worldwide without affecting safety.

The need for adding preservatives to vaccines can be reduced or obviated by making and using only single-dose vaccine formulations. However, use of single-dose preservative-free formulations raises the overall cost of vaccination and jeopardizes the effectiveness of immunization programs in developing countries. In addition, removing preservatives from multi-dose vials altogether is not viewed as a preferred option, especially in countries with limited cold storage and suboptimal standards of health care (Drain et al., *Bull World Health Organ* 81(10): 726-731 (2003). In 1928, twelve out of 21 children inoculated with contaminated diphtheria vaccine died of multiple staphylococcal abscesses and toxemia (Wilson, *The Hazards of Immunization*, Athlone Press, London. pp. 75-78 (1967). Thus, although multi-dose vials appear to be most appropriate for the production of less expensive vaccines, it is desirable to formulate multi-dose vaccines with at least one preservative to protect subjects from micro-organisms inadvertently introduced into the vaccine during multiple uses or after one or more non-sterile events. The efficacy of preservatives in resisting bacterial and other micro-organism contaminations must be balanced, however, with the effect that a particular preservative has on the immunogenicity as well as on the long term stability of each different antigenic determinant in an immunogenic composition of choice. The compatibility of Prev(e)nar 13 formulations with preservatives has not been previously addressed. It would be desirable to have an optimized formulation comprising at least one preservative that protects and/or stabilizes antigenic determinants of the pneumococcal antigen serotypes present in Prev(e)nar 13.

SUMMARY OF THE INVENTION

In a first aspect, the present invention provides a multivalent immunogenic composition comprising a plurality of capsular polysaccharides from *Streptococcus pneumoniae* serotypes and 2-phenoxyethanol (2-PE). In certain embodiments, the capsular polysaccharides are from one or more of the *Streptococcus pneumoniae* serotypes selected from 1, 3, 4, 5, 6A, 6B, 7F, 9V, 14, 18C, 19A, 19F and 23F. In certain embodiments, capsular polysaccharides are from seven or more of the *Streptococcus pneumoniae* serotypes selected from 1, 3, 4, 5, 6A, 6B, 7F, 9V, 14, 18C, 19A, 19F and 23F. In certain embodiments, capsular polysaccharides are from each of the *Streptococcus pneumoniae* serotypes 1, 3, 4, 5, 6A, 6B, 7F, 9V, 14, 18C, 19A, 19F and 23F.

In certain embodiments of the invention, the composition comprises 2-PE at a concentration of between 7 mg/mL and 15 mg/mL, about 10 mg/mL, not less than 7 mg/mL, not less than 10 mg/mL, or not less than 15 mg/mL.

Immunogenic compositions of the invention may, in certain embodiments, further comprises one or more of an adjuvant, a buffer, a cryoprotectant, a salt, a divalent cation, a non-ionic detergent, and an inhibitor of free radical oxidation. In certain embodiments, the adjuvant is aluminum phosphate.

A preferred multivalent immunogenic composition of the invention is a formulation of pneumococcal capsular polysaccharides from serotypes 1, 3, 4, 5, 6A, 6B, 7F, 9V, 14, 18C, 19A, 19F and 23F, individually conjugated to $CRM_{197}$, wherein the multivalent immunogenic composition is formulated in a sterile liquid to comprise: about 4.4 μg/mL of each polysaccharide, except for 6B at about 8.8 μg/mL; about 58 μg/mL $CRM_{197}$ carrier protein; about 0.25 mg/mL of elemental aluminum in the form of aluminum phosphate; about 0.85% sodium chloride; about 0.02% polysorbate 80; about 5 mM sodium succinate buffer at a pH of 5.8; and about 10 mg/mL of 2-phenoxyethanol.

In certain embodiments of the invention, the antigenicity of the immunogenic composition is stable for not less than 1 year, 1.5 years, 2 years or 2.5 years at a temperature of 2-8° C., 20-25° C., or 37° C.

In certain embodiments of the invention, following the inoculation of the immunogenic composition with one or more micro-organisms, the concentration of said micro-organisms is reduced over time. In certain embodiments, following inoculation with one or more bacteria strains, the composition presents at least 1.0 log reduction from the initial micro-organism count at 24 hours, at least 3.0 log reduction at 7 days from the previous value measured and not more than 0.5 log increase after 28 days, from the previous value measured. In certain embodiments, following inoculation with one or more bacteria strains, the composition presents at least 2.0 log reduction from the initial calculated count at 6 hours after inoculation, at least 3.0 log reduction from the previous value measured at 24 hours and no recovery at 28 days. Micro-organism strains include one or more strains selected from *P. aeruginosa, S. aureus, E. coli* and *B. subtilis.*

In certain embodiments, the immunogenic composition is inoculated multiple times. In certain embodiments, a second inoculation occurs at 6 hours following the initial inoculation, a third inoculation occurs at 24 hours following the initial inoculation, a third inoculation occurs as 7 days following the initial inoculation and a fourth inoculation occurs at 14 days following the initial inoculation.

In a second aspect, the present invention also provides a vial containing a multivalent immunogenic composition of the invention. A vial may contain a single dose or more than one dose of the immunogenic composition. The invention also provides a pre-filled vaccine delivery device comprising a multivalent immunogenic composition of the invention. In certain embodiments, the pre-filled vaccine delivery device is or comprises a syringe. Vaccine delivery devices of the invention may comprise a dual or multiple chamber syringe or vials or combinations thereof. In certain embodiments, the pre-filled vaccine delivery device comprises a multivalent immunogenic composition formulated for intramuscular or subcutaneous injection.

In a third aspect, the present invention also provides a kit for preparing a multivalent immunogenic composition of the invention, wherein the kit comprises (i) a plurality of capsular polysaccharides in a lyophilized form of the composition, and (ii) aqueous material for reconstituting component (i) in order to provide the aqueous composition.

In a fourth aspect, the present invention provides a multi-dose vaccine comprising four doses of a vaccine in a vial, each dose comprising from 4 to 20 mg/mL, preferably 10 mg/mL of 2-phenoxyethanol, wherein a dose is 0.5 mL of vaccine.

In a fifth aspect, the present invention also provide a method for measuring the efficacy of a vaccine formulation comprising one or more select preservative agents in the presence of some or all of the immunogenic and non-immunogenic components of the vaccine composition, wherein the test comprises at least two steps of inoculating the test composition with a select micro-organism population and comparing the log reduction of inoculated micro-organism(s) over time and under particular environmental conditions (e.g., temperature) to the log reduction in a control composition lacking the test preservative(s).

BRIEF DESCRIPTION OF THE DRAWINGS

FIG. 1—Effectiveness of Thimerosal as a vaccine preservative in various formulations.

FIG. 2—Effectiveness and stability of 2-phenoxyehtanol (2-PE) as a vaccine preservative in various formulations and at various concentrations.

FIG. 12—Non-linear regression analysis of *S. aureus* decay in various challenge studies.

FIG. 13—Comparison of 2-PE and Thimerosal as a vaccine preservative against single or multiple challenges of micro-organisms: Passing or failing EP 5.1.3 criteria B.

DETAILED DESCRIPTION OF THE INVENTION

Figure 3:
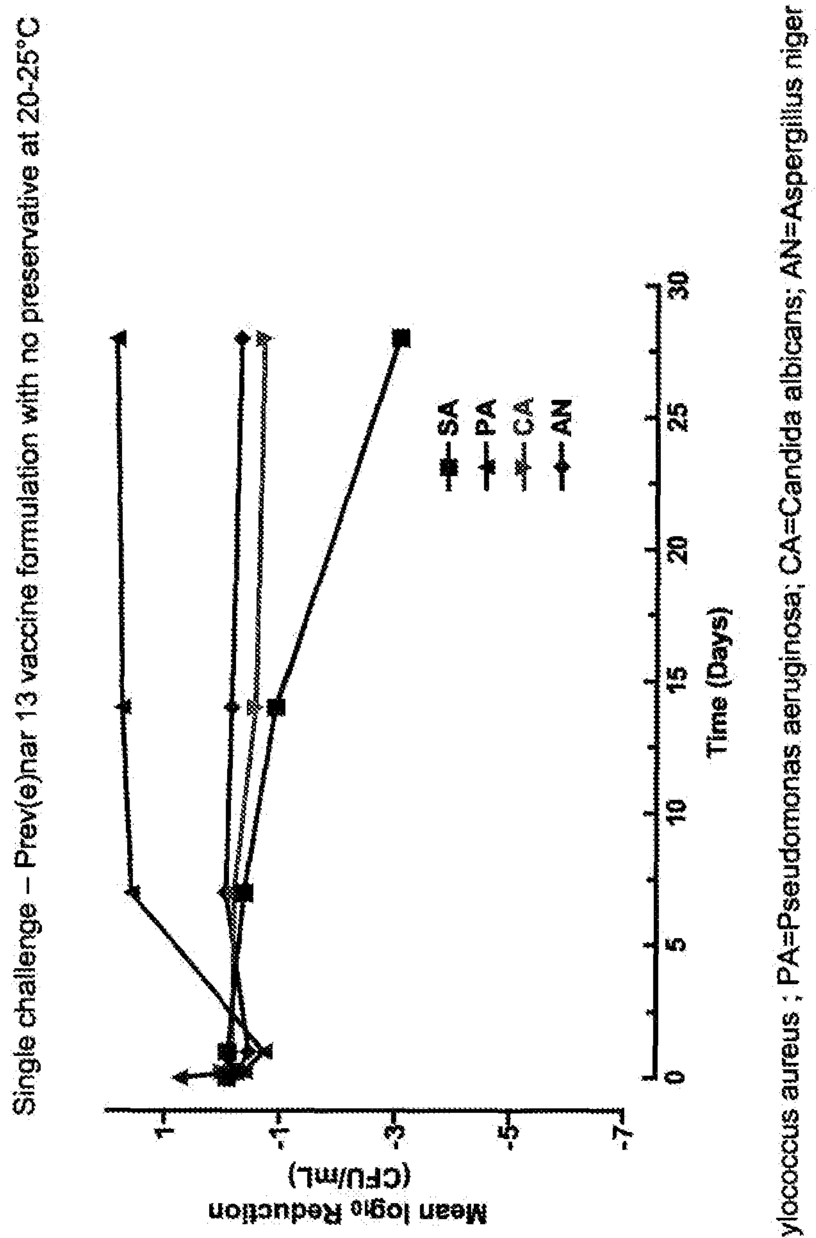
FIG. 3—Time course of micro-organism colony count reduction in Prev(e)nar 13 vaccine formulation with no preservative at 20-25° C. after a single challenge of micro-organisms (expressed as mean $\log_{10}$ change compared to time of challenge at t=0, 6 hours, 24 hours, 7 days, 14 days and 28 days).

Percentage concentration, as used in this application, is weight to volume (w/v) or weight to weight (w/w).

Unless specified otherwise, "dose" refers to a vaccine dose of 0.5 mL.

The term "multi-dose" refers to a composition which comprises more than one dose of vaccine, which may be administered to one subject or more than one subject in different administration steps and over time.

The present invention provides a multivalent immunogenic composition comprising a plurality of capsular polysaccharides from *Streptococcus pneumoniae* (also known as pneumococcus) serotypes and a preservative. This composition may be also be referred to as a vaccine and be used to induce an immune response against pneumococcus and to protect against infection in a subject, e.g., a human subject, preferably a human child or infant.

A plurality of any *Streptococcus pneumoniae* capsular polysaccharides is suitable for the composition of the present invention. In certain embodiments of the invention, the multivalent immunogenic composition comprises capsular polysaccharides prepared from serotypes 4, 6B, 9V, 14, 18C, 19F and 23F of *Streptococcus pneumoniae*. In certain embodiments, the capsular polysaccharides are prepared from serotypes 4, 6B, 9V, 14, 18C, 19F, 23F and at least one additional serotype of *Streptococcus pneumoniae*. In certain embodiments, the capsular polysaccharides are prepared from at least 4, at least 5, at least 6, at least 7, at least 8, or at least 9 serotypes selected from serotypes 1, 4, 5, 6B, 7F, 9V, 14, 18C, 19F and 23F of *Streptococcus pneumoniae*. In certain embodiments, the capsular polysaccharides are prepared from serotypes 1, 3, 4, 5, 6A, 6B, 7F, 9V, 14, 18C, 19A, 19F and 23F of *Streptococcus pneumoniae*. Capsular polysaccharides of the invention are prepared from serotypes of *Streptococcus pneumoniae* using known techniques. See, e.g., International Patent Applications WO2006/110381; WO2008/079653; WO2008/079732 and WO2008/143709, each of which is incorporated herein by reference.

In certain embodiments of the invention, the capsular polysaccharides are conjugated to a carrier protein. These pneumococcal conjugates may be prepared separately. For example, in one embodiment, each pneumococcal polysaccharide serotype is grown in a soy-based medium. The individual polysaccharides are then purified through centrifugation, precipitation, ultra-filtration and column chromatography. The purified polysaccharides are chemically activated so that the saccharides are capable of reacting with the selected carrier protein to form pneumococcal conjugates.

Once activated, each capsular polysaccharide is separately conjugated to a carrier protein to form a glycoconjugate. In certain embodiments, each different capsular polysaccharide is conjugated to the same carrier protein. In such embodiments, conjugation may be accomplished by, e.g., reductive amination.

The chemical activation of the polysaccharides and subsequent conjugation to the carrier protein are achieved by conventional means. See, for example, U.S. Pat. Nos. 4,673,574 and 4,902,506, incorporated herein by reference.

Carrier proteins are preferably proteins that are non-toxic and non-reactogenic and obtainable in sufficient amount and purity. Carrier proteins should be amenable to standard conjugation procedures. In certain embodiments of the present invention, $CRM_{197}$ is used as the carrier protein.

$CRM_{197}$ (Pfizer, Sanford, N.C.) is a non-toxic variant (i.e., toxoid) of diphtheria toxin isolated from cultures of *Corynebacterium diphtheria* strain C7 ($CRM_{197}$) grown in casamino acids and yeast extract-based medium. $CRM_{197}$ is purified through ultra-filtration, ammonium sulfate precipitation, and ion-exchange chromatography. Alternatively, $CRM_{197}$ is prepared recombinantly in accordance, e.g., with U.S. Pat. No. 5,614,382, which is hereby incorporated by reference. Other diphtheria toxoids are also suitable for use as carrier proteins.

Other suitable carrier proteins include inactivated bacterial toxins such as tetanus toxoid, pertussis toxoid, cholera toxoid (e.g., as described in International Patent Application WO2004/083251), *E. coli* LT, *E. coli* ST, and exotoxin A from *Pseudomonas aeruginosa*. Bacterial outer membrane proteins such as outer membrane complex c (OMPC), porins, transferrin binding proteins, pneumolysin, pneumococcal surface protein A (PspA), pneumococcal adhesin protein (PsaA), C5a peptidase from Group A or Group B *streptococcus*, or *Haemophilus influenzae* protein D, can also be used. Other proteins, such as ovalbumin, keyhole limpet hemocyanin (KLH), bovine serum albumin (BSA) or purified protein derivative of tuberculin (PPD) can also be used as carrier proteins.

After conjugation of the capsular polysaccharide to the carrier protein, the polysaccharide-protein conjugates are purified (i.e., enriched with respect to the amount of polysaccharide-protein conjugate) by a variety of techniques. These techniques include concentration/diafiltration operations, precipitation/elution, column chromatography, and depth filtration.

As discussed in more detail below, immunogenic compositions of the present invention comprise at least one preservative useful for producing multi-dose vaccine formulations having advantageous properties with respect to long term stability of one or more antigenic determinants of the multivalent pneumococcal capsular polysaccharide-protein conjugates and which advantageously protect the compositions from contamination by conferring resistance to one or more micro-organisms prior to administration to a subject in need thereof.

Additional formulation of the preservative-containing immunogenic composition of the present invention may be accomplished using art-recognized methods. For instance, the thirteen individual pneumococcal conjugates may be formulated with a physiologically acceptable vehicle to prepare the composition. Examples of such vehicles include, but are not limited to, water, buffered saline, polyols (e.g., glycerol, propylene glycol, liquid polyethylene glycol) and dextrose solutions, as described in more detail below.

The immunogenic compositions of the invention comprise one or more preservatives in addition to a plurality of pneumococcal capsular polysaccharide-protein conjugates. The FDA requires that biological products in multiple-dose (multi-dose) vials contain a preservative, with only a few exceptions. Vaccine products containing preservatives include vaccines containing benzethonium chloride (anthrax), 2-phenoxyethanol (DTaP, HepA, Lyme, Polio (parenteral)), phenol (Pneumo, Typhoid (parenteral), Vaccinia) and thimerosal (DTaP, DT, Td, HepB, Hib, Influenza, JE, Mening, Pneumo, Rabies). Preservatives approved for use in injectable drugs include, e.g., chlorobutanol, m-cresol, methylparaben, propylparaben, 2-phenoxyethanol, benzethonium chloride, benzalkonium chloride, benzoic acid, benzyl alcohol, phenol, thimerosal and phenylmercuric nitrate.

Having tested a variety of potentially suitable formulations comprising a preservative for enhanced effectiveness and stability of Prev(e)nar 13 immunogenic compositions, the invention disclosed herein provides such pneumococcal immunogenic compositions comprising 2-phenoxyethanol (2-PE) at a concentration of about 2.5-10 mg/dose (0.5-2%). In certain embodiments, the concentration of 2-PE is about 3.5-7.5 mg/dose (0.7-1.5%). In certain embodiments, the concentration of 2-PE is about 5 mg/dose (1%). In certain embodiments, the concentration of 2-PE is not less than 3.5 mg/dose (0.7%), not less than 4.0 mg/dose (0.8%), not less than 4.5 mg/dose (0.9%), not less than 5.0 mg/dose (1%), not less than 5.5 mg/dose (1.1%), not less than 6.0 mg/dose (1.2%), not less than 6.5 mg/dose (1.3%), not less than 7.0 mg/dose, not less than 7.5 mg/dose (1.5%), not less than 8.0 mg/dose (1.6%), not less than 9.0 mg/dose (1.8%) or not less than 10 mg/dose (2%).

In certain embodiments of the invention, the pneumococcal immunogenic compositions contain one or more additional preservatives including, but not limited to, Thimerosal and formalin.

In certain embodiments, the immunogenic composition may comprise one or more adjuvants. As defined herein, an "adjuvant" is a substance that serves to enhance the immunogenicity of an immunogenic composition of this invention. Thus, adjuvants are often given to boost the immune response and are well known to the skilled artisan. Suitable adjuvants to enhance effectiveness of the composition include, but are not limited to:

(1) aluminum salts (alum), such as aluminum hydroxide, aluminum phosphate, aluminum sulfate, etc.;

(2) oil-in-water emulsion formulations (with or without other specific immuno-stimulating agents such as muramyl peptides (defined below) or bacterial cell wall components), such as, for example, (a) MF59 (PCT Application WO 90/14837), containing 5% Squalene, 0.5% Tween 80, and 0.5% Span 85 (optionally containing various amounts of MTP-PE (see below, although not required)) formulated into submicron particles using a microfluidizer such as Model 110Y microfluidizer (Microfluidics, Newton, Mass.), (b) SAF, containing 10% Squalene, 0.4% Tween 80, 5% pluronic-blocked polymer L121, and thr-MDP (see below) either microfluidized into a submicron emulsion or vortexed to generate a larger particle size emulsion, and (c) Ribi adjuvant system (RAS), (Corixa, Hamilton, Mont.) containing 2% Squalene, 0.2% Tween 80, and one or more bacterial cell wall components from the group consisting of 3-O-deaylated monophosphorylipid A (MPL) described in U.S. Pat. No. 4,912,094 (Corixa), trehalose dimycolate (TDM), and cell wall skeleton (CWS), preferably MPL+CWS (Detox);

(d) Polysorbate 80 (Tween 80);

(3) saponin adjuvants, such as Quil A or STIMULON QS-21 (Antigenics, Framingham, Mass.) (U.S. Pat. No. 5,057,540) may be used or particles generated therefrom such as ISCOMs (immuno-stimulating complexes);

(4) bacterial lipopolysaccharides, synthetic lipid A analogs such as aminoalkyl glucosamine phosphate compounds (AGP), or derivatives or analogs thereof, which are available from Corixa, and which are described in U.S. Pat. No. 6,113,918; one such AGP is 2-[(R)-3-Tetradecanoyloxytetradecanoylamino]ethyl 2-Deoxy-4-O-phosphono-3-O—[(R)-3-tetradecanoyloxytetradecanoyl]-2-[(R)-3-tetradecanoyloxytetradecanoylamino]-b-D-glucopyranoside, which is also know as 529 (formerly known as RC529), which is formulated as an aqueous form or as a stable emulsion, synthetic polynucleotides such as oligonucleotides containing CpG motif(s) (U.S. Pat. No. 6,207,646);

(5) cytokines, such as interleukins (e.g., IL-1, IL-2, IL-4, IL-5, IL-6, IL-7, IL-12, IL-15, IL-18, etc.), interferons (e.g., gamma interferon), granulocyte macrophage colony stimulating factor (GM-CSF), macrophage colony stimulating factor (M-CSF), tumor necrosis factor (TNF), costimulatory molecules B7-1 and B7-2, etc.;

(6) detoxified mutants of a bacterial ADP-ribosylating toxin such as a cholera toxin (CT) either in a wild-type or mutant form, for example, where the glutamic acid at amino acid position 29 is replaced by another amino acid, preferably a histidine, in accordance with published international patent application number WO 00/18434 (see also WO 02/098368 and WO 02/098369), a pertussis toxin (PT), or an *E. coli* heat-labile toxin (LT), particularly LT-K63, LT-R72, CT-S109, PT-K9/G129 (see, e.g., WO 93/13302 and WO 92/19265); and (7) other substances that act as immuno-stimulating agents to enhance the effectiveness of the composition, such as calcium salt, iron, zinc, acylated tyrosine suspension, acylated sugar, derivatized sugars/saccharides, polyphosphazenes, biodegradable microspheres, monophosphoryl lipid A (MPL), lipid A derivatives (e.g. of reduced toxicity), 3-O-deacylated MPL, quil A, Saponin, QS21, tocol, Freund's Incomplete Adjuvant (Difco Laboratories, Detroit, Mich.), Merck Adjuvant 65 (Merck and Company, Inc., Rahway, N.J.), AS-2 (Smith-Kline Beecham, Philadelphia, Pa.), CpG oligonucleotides (preferably unmethylated), bioadhesives and mucoadhesives, microparticles, liposomes, polyoxyethylene ether formulations, polyoxyethylene ester formulations, and muramyl peptides or imidazoquinolone compounds. Muramyl peptides include, but are not limited to, N-acetyl-muramyl-L-threonyl-D-isoglutamine (thr-MDP), N-acetyl-normuramyl-L-alanine-2-(1'-2' dipalmitoyl-sn-glycero-3-hydroxyphosphoryloxy)-ethylamine (MTP-PE), and the like.

In certain embodiments, the adjuvant composition is one which favors induction of TH1-type cytokines (e.g. IFN-γ, TNFα, IL-2 and IL-12) to a greater extent than TH2-type cytokines, which may favor the induction of cell mediated immune responses to an administered antigen. Particular adjuvant systems which promote a predominantly TH1 response include but are not limited to lipid A derivatives, such as Monophosphoryl lipid A (MPL) or its derivatives, e.g. 3-de-O-acylated MPL (3D-MPL), a combination of MPL and/or 3D-MPL and an aluminum salt and/or a saponin derivative (e.g., QS21 in combination with 3D-MPL as disclosed in WO 94/00153, or QS21 and cholesterol as disclosed in WO 96/33739), triterpenoids, and oil-in-water emulsions such as one comprising tocopherol (as disclosed in WO 95/17210).

An adjuvant may optionally be adsorbed by or combined with one or more of the immunogenic components of the preserved vaccine formulation of the invention. As used herein, the term "adsorbed antigen" refers to a mixture in which greater than 20%, 30%, 40%, 50%, 60%, 70%, 80%, or 90% of an antigen is adsorbed to adjuvant. In certain embodiments, the adjuvant is adsorbed aluminum (Al+) phosphate or aluminum hydroxyphosphate. Typically, the total aluminum content is 200-1000 μg, 300-900 μg, 400-800 μg, 500-700 μg or around 630 μg Al+ per 0.5 mL dose, which may be all aluminum hydroxide or all aluminum phosphate. Alternatively Al+ content may be from a mixture of aluminum hydroxide and aluminum phosphate in various ratios, e.g., 1:8-8:1, 1:4-4:1, 3:8-8:3, 1:2-2:1 or 1:1 of aluminum phosphate: aluminum hydroxide. Although most aluminum is provided by preadsorbed antigens before mixture to form a combination vaccine, some aluminum may be added in free form during formulation of the combination vaccine of the invention, e.g. before the pH adjustment step described herein. Typically, free aluminum content per 0.5 mL dose may be 0-300 μg, 50-250 μg, 75-200 μg, 100-150 μg or around 120 μg of Al3+. Free Al3+ may be all Al(OH)3 or all AlPO4, or a mixture of Al(OH) 3 and AlPO4 in various ratios.

Vaccine antigenic components may be preadsorbed onto an aluminum salt individually prior to mixing. In another embodiment, a mix of antigens may be preadsorbed prior to mixing with further adjuvants. Alternatively certain components of the vaccines of the invention may be formulated but not intentionally adsorbed onto adjuvant.

Formulations of the invention may further comprise one or more of a buffer, a salt, a divalent cation, a non-ionic detergent, a cryoprotectant such as a sugar, and an anti-oxidant such as a free radical scavenger or chelating agent, or any multiple combination thereof. The choice of any one component, e.g., a chelator, may determine whether or not another component (e.g., a scavenger) is desirable. The final composition formulated for administration should be sterile and/or pyrogen free. The skilled artisan may empirically determine which combinations of these and other components will be optimal for inclusion in the preservative containing vaccine compositions of the invention depending on a variety of factors such as the particular storage and administration conditions required.

In certain embodiments, a formulation of the invention which is compatible with parenteral administration comprises one or more physiologically acceptable buffers selected from, but not limited to, Tris(trimethamine), phosphate, acetate, borate, citrate, glycine, histidine and succinate. In certain embodiments, the formulation is buffered to within a pH range of about 6.0 to about 9.0, preferably from about 6.4 to about 7.4.

In certain embodiments, it may be desirable to adjust the pH of the immunogenic composition or formulation of the invention. The pH of a formulation of the invention may be adjusted using standard techniques in the art. The pH of the formulation may be adjusted to be between 3.0 and 8.0. In certain embodiments, the pH of the formulation may be, or may adjusted to be, between 3.0 and 6.0, 4.0 and 6.0, or 5.0 and 8.0. In other embodiments, the pH of the formulation may be, or may adjusted to be, about 3.0, about 3.5, about 4.0, about 4.5, about 5.0, about 5.5, about 5.8, about 6.0, about 6.5, about 7.0, about 7.5, or about 8.0. In certain embodiments, the pH may be, or may adjusted to be, in a range from 4.5 to 7.5, or from 4.5 to 6.5, from 5.0 to 5.4, from 5.4 to 5.5, from 5.5 to 5.6, from 5.6 to 5.7, from 5.7 to 5.8, from 5.8 to 5.9, from 5.9 to 6.0, from 6.0 to 6.1, from 6.1 to 6.2, from 6.2 to 6.3, from 6.3 to 6.5, from 6.5 to 7.0, from 7.0 to 7.5 or from 7.5 to 8.0. In a specific embodiment, the pH of the formulation is about 5.8.

In certain embodiments, a formulation of the invention which is compatible with parenteral administration comprises one or more divalent cations, including but not limited to $MgCl_2$, $CaCl_2$ and $MnCl_2$, at a concentration ranging from about 0.1 mM to about 10 mM, with up to about 5 mM being preferred.

In certain embodiments, a formulation of the invention which is compatible with parenteral administration comprises one or more salts, including but not limited to sodium chloride, potassium chloride, sodium sulfate, and potassium sulfate, present at an ionic strength which is physiologically acceptable to the subject upon parenteral administration and included at a final concentration to produce a selected ionic strength or osmolarity in the final formulation. The final ionic strength or osmolality of the formulation will be determined by multiple components (e.g., ions from buffering compound(s) and other non-buffering salts. A preferred salt, NaCl, is present from a range of up to about 250 mM, with salt concentrations being selected to complement other components (e.g., sugars) so that the final total osmolarity of the formulation is compatible with parenteral administration (e.g., intramuscular or subcutaneous injection) and will promote long term stability of the immunogenic components of the vaccine formulation over various temperature ranges. Salt-free formulations will tolerate increased ranges of the one or more selected cryoprotectants to maintain desired final osmolarity levels.

In certain embodiments, a formulation of the invention which is compatible with parenteral administration comprises one or more cryoprotectants selected from but not limited to disaccharides (e.g., lactose, maltose, sucrose or trehalose) and polyhydroxy hydrocarbons (e.g., dulcitol, glycerol, mannitol and sorbitol).

In certain embodiments, the osmolarity of the formulation is in a range of from about 200 mOs/L to about 800 mOs/L, with a preferred range of from about 250 mOs/L to about 500 mOs/L, or about 300 mOs/L-about 400 mOs/L. A salt-free formulation may contain, for example, from about 5% to about 25% sucrose, and preferably from about 7% to about 15%, or about 10% to about 12% sucrose. Alternatively, a salt-free formulation may contain, for example, from about 3% to about 12% sorbitol, and preferably from about 4% to 7%, or about 5% to about 6% sorbitol. If salt such as sodium chloride is added, then the effective range of sucrose or sorbitol is relatively decreased. These and other such osmolality and osmolarity considerations are well within the skill of the art.

In certain embodiments, a formulation of the invention which is compatible with parenteral administration comprises one or more free radical oxidation inhibitors and/or chelating agents. A variety of free radical scavengers and chelators are known in the art and apply to the formulations and methods of use described herein. Examples include but are not limited to ethanol, EDTA, a EDTA/ethanol combination, triethanolamine, mannitol, histidine, glycerol, sodium citrate, inositol hexaphosphate, tripolyphosphate, ascorbic acid/ascorbate, succinic acid/succinate, malic acid/maleate, desferal, EDDHA and DTPA, and various combinations of two or more of the above. In certain embodiments, at least one non-reducing free radical scavenger may be added at a concentration that effectively enhances long term stability of the formulation. One or more free radical oxidation inhibitors/chelators may also be added in various combinations, such as a scavenger and a divalent cation. The choice of chelator will determine whether or not the addition of a scavenger is needed.

In certain embodiments, a formulation of the invention which is compatible with parenteral administration comprises one or more non-ionic surfactants, including but not limited to polyoxyethylene sorbitan fatty acid esters, Polysorbate-80 (Tween 80), Polysorbate-60 (Tween 60), Polysorbate-40 (Tween 40) and Polysorbate-20 (Tween 20), polyoxyethylene alkyl ethers, including but not limited to Brij 58, Brij 35, as well as others such as Triton X-100; Triton X-114, NP40, Span 85 and the Pluronic series of non-ionic surfactants (e.g., Pluronic 121), with preferred components Polysorbate-80 at a concentration from about 0.001% to about 2% (with up to about 0.25% being preferred) or Polysorbate-40 at a concentration from about 0.001% to 1% (with up to about 0.5% being preferred).

In certain embodiments, a formulation of the invention comprises one or more additional stabilizing agents suitable for parenteral administration, e.g., a reducing agent comprising at least one thiol (—SH) group (e.g., cysteine, N-acetyl cysteine, reduced glutathione, sodium thioglycolate, thiosulfate, monothioglycerol, or mixtures thereof). Alternatively or optionally, preservative-containing vaccine formulations of the invention may be further stabilized by removing oxygen from storage containers, protecting the formulation from light (e.g., by using amber glass containers).

Preservative-containing vaccine formulations of the invention may comprise one or more pharmaceutically acceptable carriers or excipients, which includes any excipient that does not itself induce an immune response. Suitable excipients include but are not limited to macromolecules such as proteins, saccharides, polylactic acids, polyglycolic acids, polymeric amino acids, amino acid copolymers, sucrose (Paoletti et al, 2001, *Vaccine,* 19:2118), trehalose, lactose and lipid aggregates (such as oil droplets or liposomes). Such carriers are well known to the skilled artisan. Pharmaceutically acceptable excipients are discussed, e.g., in Gennaro, 2000, Remington: The Science and Practice of Pharmacy, $20^{th}$ edition, ISBN:0683306472.

Compositions of the invention may be lyophilized or in aqueous form, i.e. solutions or suspensions. Liquid formulations may advantageously be administered directly from their packaged form and are thus ideal for injection without the need for reconstitution in aqueous medium as otherwise required for lyophilized compositions of the invention.

In particular embodiments of the present invention, the vaccine is a multivalent immunogenic composition comprising one or more pneumococcal capsular polysaccharides selected from serotypes 1, 3, 4, 5, 6A, 6B, 7F, 9V, 14, 18C, 19A, 19F and 23F, individually conjugated to $CRM_{197}$. The vaccine is formulated to comprise: from 1 to 5 μg, preferably about 4.4 μg/mL of each polysaccharide but preferably about 8.8 μg/mL of 6B; from 20 to 100 μg/mL, preferably about 58 μg/mL $CRM_{197}$ carrier protein; from 0.02 to 2 mg/mL, preferably 0.25 mg/mL of elemental aluminum in the form of aluminum phosphate; from 0.5 to 1.25%, preferably about 0.85% sodium chloride; from 0.002 to 0.2%, preferably about 0.02% polysorbate 80; from 1 to 10 mM, preferably about 5 mM sodium succinate buffer at a pH from 4 to 7, preferably at a pH of 5.8; and from 4 to 20 mg/mL, preferably about 10 mg/mL of 2-phenoxyethanol.

In certain preferred embodiments of the present invention, the vaccine is a multivalent immunogenic composition comprising pneumococcal capsular polysaccharides from serotypes 1, 3, 4, 5, 6A, 6B, 7F, 9V, 14, 18C, 19A, 19F and 23F, individually conjugated to $CRM_{197}$. The vaccine is formulated to comprise: about 4.4 μg/mL of each saccharide, except for 6B at about 8.8 μg/mL; about 58 μg/mL $CRM_{197}$ carrier protein; about 0.25 mg/mL of elemental aluminum in the form of aluminum phosphate; about 0.85% sodium chloride; about 0.02% polysorbate 80; about 5 mM sodium succinate buffer at a pH of 5.8; and about 10 mg/mL of 2-phenoxyethanol.

The amount of many of the materials which the composition of the invention may comprise can be expressed as weight/dose, weight/volume, or concentration (as weight/volume or weight/weight). All of these values may be converted from one to another. For conversions to and from a weight/dose unit, a volume of the dose is specified. For example, given a dose of 0.5 mL, 5.0 mg/dose 2-PE is equivalent to a concentration of 10 mg/mL or 1.0% (g/100 mL).

The formulation of the vaccine may also be expressed as a ratio of polysaccharide:2-PE. For example, a 0.5 mL dose of the preferred formulation of 4.4 μg/mL of each saccharide, except for 6B at 8.8 μg/mL, and 10 mg/mL 2-PE will have 30.8 μg polysaccharide (2.2 μg×12 serotypes+4.4 μg for serotype 6B) and 5000 μg 2-PE. Therefore the weight ratio of polysaccharide:2-PE is 30.8:5000.

In certain embodiments of the invention, the polysaccharide:2-PE weight ratio of the vaccine is from 5:5000 to 100:5000. In a preferred embodiment of the invention, said polysaccharide:2-PE weight ratio is about 30.8:5000.

Delivery of Vaccine Formulations

Also provided are methods of using the disclosed pharmaceutical compositions and formulations comprising at least one preservative to induce an immune response against pneumococcus in a mammalian subject, such as a human subject, preferably in a child or infant, and to thereby protect against infection. The vaccine formulations of the present invention may be used to protect a human subject susceptible to pneumococcal infection, by administering the vaccine via a systemic or mucosal route. These administrations may include, e.g., parenteral administration or mucosal administration to the oral/alimentary, respiratory or genitourinary tracts.

Direct delivery of vaccine preparations of the present invention to a subject may be accomplished by parenteral administration (intramuscularly, intraperitoneally, intradermally, subcutaneously, intravenously, or to the interstitial space of a tissue); or by rectal, oral, vaginal, topical, transdermal, intranasal, ocular, aural, pulmonary or other mucosal administration. In a preferred embodiment, parenteral administration is by intramuscular injection, e.g., to the thigh or upper arm of the subject. Injection may be via a needle (e.g. a hypodermic needle), but needle free injection may alternatively be used. A typical intramuscular dose is 0.5 mL. Compositions of the invention may be prepared in various forms, e.g., for injection either as liquid solutions or suspensions. In certain embodiments, the composition may be prepared as a powder or spray for pulmonary administration, e.g. in an inhaler. In other embodiments, the composition may be prepared as a suppository or pessary, or for nasal, aural or ocular administration, e.g. as a spray, drops, gel or powder.

In one embodiment, intranasal administration may be used for prevention of pneumonia or otitis media (as nasopharyngeal carriage of pneumococci can be more effectively prevented, thus attenuating infection at its earliest stage).

The amount of conjugate in each vaccine dose is selected as an amount that induces an immunoprotective response without significant, adverse effects. Such amount can vary depending upon the pneumococcal serotype. Generally, each dose will comprise 0.1 to 100 μg of polysaccharide, particularly 0.1 to 10 μg, and more particularly 1 to 5 μg.

Optimal amounts of components for a particular vaccine may be ascertained by standard studies involving observation of appropriate immune responses in subjects. Following an initial vaccination, subjects can receive one or several booster immunizations adequately spaced.

The routine schedule for infants and toddlers against invasive disease caused by *S. Pneumoniae* due to the serotypes included in the Prev(e)nar 13 vaccine is 2, 4, 6 and 12-15 months of age. Compositions of the present invention are also suitable for use with older children, adolescents, teens and adults in which the same or different routine schedules may apply, as determined by the skilled professional.

Packaging and Dosage Forms

Vaccines of the invention may be packaged in unit dose or multi-dose form (e.g. 2 doses, 4 doses, or more). For multi-dose forms, vials are typically but not necessarily preferred over pre-filled syringes. Suitable multi-dose formats include but are not limited to: 2 to 10 doses per container at 0.1 to 2 mL per dose. In certain embodiments, the dose is a 0.5 mL dose. See, e.g., International Patent Application WO2007/

127668, which is incorporated by reference herein. Compositions may be presented in vials or other suitable storage containers, or may be presented in pre-filled delivery devices, e.g., single or multiple component syringes, which may be supplied with or without needles. A syringe typically but need not necessarily contains a single dose of the preservative-containing vaccine composition of the invention, although multi-dose, pre-filled syringes are also envisioned. Likewise, a vial may include a single dose but may alternatively include multiple doses.

Effective dosage volumes can be routinely established, but a typical dose of the composition for injection has a volume of 0.5 mL. In certain embodiments, the dose is formulated for administration to a human subject. In certain embodiments, the dose is formulated for administration to an adult, teen, adolescent, toddler or infant (i.e., no more than one year old) human subject and may in preferred embodiments be administered by injection.

Liquid vaccines of the invention are also suitable for reconstituting other vaccines which are presented in lyophilized form. Where a vaccine is to be used for such extemporaneous reconstitution, the invention provides a kit with two or more vials, two or more ready-filled syringes, or one or more of each, with the contents of the syringe being used to reconstitute the contents of the vial prior to injection, or vice versa.

Alternatively, vaccine compositions of the present invention may be lyophilized and reconstituted, e.g., using one of a multitude of methods for freeze drying well known in the art to form dry, regular shaped (e.g., spherical) particles, such as micropellets or microspheres, having particle characteristics such as mean diameter sizes that may be selected and controlled by varying the exact methods used to prepare them. The vaccine compositions may further comprise an adjuvant which may optionally be prepared with or contained in separate dry, regular shaped (e.g., spherical) particles such as micropellets or microspheres. In such embodiments, the present invention further provides a vaccine kit comprising a first component that includes a stabilized, dry vaccine composition, optionally further comprising one or more preservatives of the invention, and a second component comprising a sterile, aqueous solution for reconstitution of the first component. In certain embodiments, the aqueous solution comprises one or more preservatives, and may optionally comprise at least one adjuvant (see, e.g., WO2009/109550 (incorporated herein by reference).

In yet another embodiment, a container of the multi-dose format is selected from one or more of the group consisting of, but not limited to, general laboratory glassware, flasks, beakers, graduated cylinders, fermentors, bioreactors, tubings, pipes, bags, jars, vials, vial closures (e.g., a rubber stopper, a screw on cap), ampoules, syringes, dual or multi-chamber syringes, syringe stoppers, syringe plungers, rubber closures, plastic closures, glass closures, cartridges and disposable pens and the like. The container of the present invention is not limited by material of manufacture, and includes materials such as glass, metals (e.g., steel, stainless steel, aluminum, etc.) and polymers (e.g., thermoplastics, elastomers, thermoplastic-elastomers). In a particular embodiment, the container of the format is a 5 mL Schott Type 1 glass vial with a butyl stopper. The skilled artisan will appreciate that the format set forth above is by no means an exhaustive list, but merely serve as guidance to the artisan with respect to the variety of formats available for the present invention. Additional formats contemplated for use in the present invention may be found in published catalogues from laboratory equipment vendors and manufacturers such as United States Plastic Corp. (Lima, Ohio), VWR.

Methods for Evaluating Preservative Efficacy in Vaccine Compositions

The present invention further provides novel methods for measuring the efficacy of a vaccine formulation comprising one or more select preservative agents in the presence of some or all of the immunogenic and non-immunogenic components of the vaccine composition. The WHO Protocol on preservative efficacy utilizes USP and EP tests and include Open Vial Policy conditions when performing certain tests. A typical preservative efficacy test is a single challenge test in which a test composition is inoculated one time with a select micro-organism population and the log reduction of inoculated micro-organism over time and under particular environmental conditions (e.g., temperature) is compared to the log reduction of inoculated micro-organism in a control composition lacking the test preservative(s). See, e.g., Examples 2 and 3, below. However, no additional tests have been required to address preservative efficacy upon multiple contaminations, e.g., to address vials and stoppers by inoculating the same vials multiple times.

Accordingly, the invention provides a multi-challenge test for evaluating the efficacy of one or more preservatives in an immunogenic composition, wherein the test comprises at least two steps of inoculating the test composition with a select micro-organism population and comparing the reduction of inoculated micro-organism(s) over time and under particular environmental conditions (e.g., temperature) to the reduction in a control composition lacking the test preservative(s). See Examples 4 and 5, below.

Preservative Effectiveness

Preservative-containing vaccine formulations of the present invention are suitable for filling in a multi-dose vaccine vial or container compatible with, e.g., parenteral administration, and remain stable for extended periods of time at 2-8° C., room temperature or 37° C. with reduced or negligible loss of activity when compared to the same formulation lacking preservative(s).

The amount of preservative in the formulation is selected to be an amount that fulfills requirements for vaccine safety, as defined by the United States (U.S.), European or World Health Organization (WHO) Pharmacopeias, or a combination thereof.

For ascertaining preservative levels according to U.S. and European Pharmacopeias (USP and EP, respectively), the vaccine formation is inoculated once with approximately $10^5$ to $10^6$ CFU/ml at time 0 (CFU=colony forming units) of:

1. *Staphylococcus aureus* (Bacteria; ATCC #6538; "SA")
2. *Pseudomonas aeruginosa* (Bacteria; ATCC #9027; "PA")
3. *Candida albicans* (Yeast; ATCC#10231; "CA")
4. *Aspergillus niger* (Mold; ATCC #16404; "AN")

To represent the worst reasonable case of contamination that may occur in practice during the repeated use of a multi-dose presentation, WHO requires safety testing with deliberate exposure to multiple contamination events using bacterial strains, *Pseudomonas Aeruginosa* ("PA"), *Staphylococcus Aureus* ("SA"), *Escherichia coli* ("EC") and *Bacillus subtilis* ("BA"). Formulations are spiked with $5\times10^3$ CFU/ml of each organism at times 0, 6 hours, 24 hours, 7 days and 14 days after initial challenge and stored either at 2-8° C. or at 22-24° C. to mimic the potential storage conditions in practice.

USP 29 NF 24 Supplement 2 (USP) requires that, after an inoculation of bacterial micro-organism(s), there is at least 1.0 log reduction from the initial calculated count (i.e., at time of inoculation) at 7 days, at least 3.0 log reduction at 14 days from the previous value measured, and no increase at 28 days compared to the previous value measured. See Table 1. For yeast and fungi, the USP requirement is for there to be no increase from time of inoculation at 7, 14 and 28 days.

EP requirements are more stringent. EP 5th Edition 5.6 (5.1.3) requirements for parenteral and ophthalmic preparations has two components: Category A and Category B. Category A (EP-A) requires, for bacteria, at least 2.0 log reduction from the initial calculated count at 6 hours after inoculation, at least 3.0 log reduction from the previous value measured at 24 hours and no recovery at 28 days. Category B (EP-B) requires, for bacteria, at least 1.0 log reduction from the initial calculated count at 24 hours, at least 3.0 log reduction at 7 days from the previous value measured and not more than 0.5 log increase from the previous value measured (i.e., no increase) at 28 days. See Table 1. For yeast and fungi, Category A requires at least 2.0 log reduction at 7 days from the initial calculated count, and no increase at 28 days from the previous measured value; and Category B requires at least 1.0 log reduction from the initial calculated count at 14 days and no increase at 28 days from the previous measured value.

TABLE 1

Acceptance Criteria for Preservative Effectiveness Test Between United States, European and Japanese Pharmacopeias

| | | Log CFU/mL reduction | | | | |
|---|---|---|---|---|---|---|
| Organisms | Method | 6 h | 24 h | 7 d | 14 d | 28 d |
| Bacteria | EP A* | 2 | 3 | — | — | NR*** |
| | EP B | — | 1 | 3 | — | NI** |
| | USP | — | — | 1 | 3 | NI |
| | JP | — | — | — | 3 | NI |
| Yeast and Fungi | EP A | — | — | 2 | — | NI |
| | EP B | — | — | — | 1 | NI |
| | USP | — | — | NI | NI | NI |
| | JP | — | — | — | NI | NI |

*The A criteria express the recommended efficacy to be achieved. In justified cases, where the A criteria can not be attained, the B criteria must be satisfied.
**NI: No increase: It is defined as not more than 0.5 $\log_{10}$ unit higher than the previous value measured.
***NR: No recovery In certain embodiments of the present invention, a preservative of the invention is effective in reducing the concentration of micro-organisms in the immunogenic formulation. In certain embodiments of the invention, the vaccine formulation, comprising at least one preservative, reduces the concentration of one or more micro-organisms following inoculation with said micro-organisms compared to the vaccine formulation without the one or more preservatives. In a particular embodiment of the invention, the formulation presents at least 1.0 log reduction from the initial micro-organism count at 24 hours, at least 3.0 log reduction at 7 days from the previous value measured and not more than 0.5 log increase at 28 days from the previous value measured. In another particular embodiment of the invention, the formulation presents at least 2.0 log reduction from the initial calculated count at 6 hours after inoculation, at least 3.0 log reduction at 24 hours from the previous value measured and no recovery at 28 days, compared from the initial micro-organism count. In another embodiment of the invention, the formulation meets European Pharmacopeia (EP) requirements for parenteral and ophthalmic preparations, in particular Category A (EP-A) and/or Category B (EP-B) of the EP 5th Edition 5.6 (5.1.3) requirements. In another embodiment of the invention, the formulation meets United States Pharmacopeia (USP) 29 NF 24 Supplement 2 requirements for parenteral preparations.

In certain embodiments of the invention, the at least one preservative of the invention is effective in reducing the concentration of micro-organisms in the formulation when challenged with micro-organisms compared to a formulation lacking the one or more preservatives. The micro-organisms may be, without limitation, one or more of the following: *Pseudomonas aeruginosa, Staphylococcus aureus, Escherichia coli, Bacillus subtilis, Candida albicans Aspergillus niger* and others.

In certain embodiments of the invention, the micro-organisms may be introduced or inoculated into the vaccine one or more times at various intervals. The inoculation may occur in the context of a deliberate experimental inoculation or in the context of a contaminated hypodermic needle entering a container of a multi-dose vaccine formulation. The interval between inoculations may be between 1 minute and 1 month. In a particular embodiment, the multiple inoculations occur, following an initial inoculation, at 6 hours following the initial inoculation, at 24 hours following the initial inoculation, at 7 days following the initial inoculation and at 14 days following the initial inoculation.

Parameters for Vaccine and Preservative Stability

In certain embodiments of the present invention, the antigenicity of at least one antigenic determinant (i.e., polysaccharide preparation from a *Streptococcus pneumoniae* serotype) in the vaccine formulation is stable for a range of storage times and temperatures. The antigenicity may be measure by methods known in the art. For example, total antigenicity may be determined by using type-specific anti-sera, as described in Example 3.

In certain embodiments of the present invention, the antigenicity of at least one antigenic determinant in the vaccine formulation is stable for not less than 4 weeks, not less than 6 weeks, not less than 8 weeks, not less than 10 weeks, not less than 12 weeks, not less than 18 weeks, not less than 24 weeks, not less than 48 weeks, not less than 1 year, not less than 1.25 years, not less than 1.5 years, not less than 1.75 years, not less than 2 years, not less than 2.25 years, or not less than 2.5 years. Preferably, the antigenicity of a plurality of antigenic determinants, e.g., at least 50%, 75%, 80%, 85%, 90%, 95% or more, of the antigenic determinants in the vaccine in the formulation are stable for not less than 4 weeks, not less than 6 weeks, not less than 8 weeks, not less than 10 weeks, not less than 12 weeks, not less than 18 weeks, not less than 24 weeks, not less than 48 weeks, not less than 1 year, not less than 1.25 years, not less than 1.5 years, not less than 1.75 years, not less than 2 years, not less than 2.25 years, or not less than 2.5 years.

In certain embodiments of the present invention, antigenicity of at least one antigenic determinant in the vaccine formulation is stable when stored at about −25° C. to about 37° C., or −20 to −10° C., or 2 to 8° C., or about room temperature, or 22° C. to 28° C., or about 37° C. In a particular embodiment of the invention, antigenicity of at least one antigenic determinant in the vaccine formulation is stable after storage for not less than 2.5 years at a temperature of 2 to 8° C.

In certain embodiments of the present invention, the concentration of the preservative of the invention is stable after storage of the vaccine at the above-mentioned durations and storage temperatures. In a particular embodiment of the invention, the concentration of the preservative in the vaccine formulation is stable after storage of the vaccine for not less than 2.5 years at a temperature of 2 to 8° C. The concentration of the preservative may be measure by methods known in the art. For example, Thimerosal may be measured using Cold Vapor Atomic Absorption Spectrometry (CVAAS), as described in Example 3. 2-EP concentration may be measured with a Reversed-Phase HPLC assay, also as described in Example 3. A Reversed-Phase HPLC assay may be performed in the following manner: Samples are vortexed and diluted 1:10 into 5 mM Succinate buffer in saline, centrifuged and diluted again 1:10 into 5 mM succinate buffer in saline (final dilution of the Test Sample is 1:100). The sample is then assayed utilizing the Agilent Eclipse XDB-C18 HPLC column and a linear gradient of water and acetonitrile containing trifluoroacetic acid. The quantification of the preservative is then compared to a standard curve. See also, Sharma et al., *Biologicals* 36(1): 61-63 (2008).

The above disclosure generally describes the present invention. A more complete understanding may be obtained by reference to the following specific examples. These examples are described solely for the purpose of illustration and are not intended to limit the scope of the invention.

EXAMPLES

Example 1

Preliminary Preservative Screening Study

Formulation development of multi-dose Prev(e)nar 13 vaccine started with preliminary screening of preservatives, including Phenol (0.25%), 2-Phenoxyethanol (5 mg/mL), Meta-Cresol (0.3%), Methylparaben and Propylparaben (0.18% and 0.12%, respectively) in Prev(e)nar 13 formulations.

To test for preservative effectiveness, aliquots of vaccine were inoculated with the following organisms:

1. *Staphylococcus aureus* (Bacteria; ATCC #6538)
2. *Pseudomonas aeruginosa* (BacteriaATCC #9027)
3. *Candida albicans* (Yeast; ATCC#10231)
4. *Aspergillus niger* (Mold; ATCC #16404)

Thirty milliliters (ml) of each vaccine formulation with and without Thimerosal or 2-PE at indicated concentrations or saline containing Thimerosal at 0.02% were inoculated in triplicates with a suspension of each test organism to achieve an inoculum density of approximately $10^5$ to $10^6$ CFU/ml at time 0 (CFU=colony forming units). The volume of each inoculum did not exceed 1% of the volume of the product during each deliberate challenge. Samples were mixed to ensure even distribution of challenged organisms. Another 30 ml of vaccine in triplicate (with and without preservative) were used as a negative control and spiked with the culture media alone to evaluate the inherent contamination that might be present in the sample or media. Each of the three series of vaccines, and positive and negative controls, was then separately incubated at 20 to 25° C. Aliquots (1 ml) of the challenged samples and controls (or their appropriate serial ten fold dilutions) were enumerated by plate count in duplicates at time 0 and at intervals of 6 hours, 24 hours, 7 days, 14 days and 28 days post-inoculation.

USP 29 NF 24 Supplement 2 (USP) requires that, after an inoculation of bacterial micro-organism(s), there is at least 1.0 log reduction from the initial calculated count (i.e., at time of inoculation) at 7 days, at least 3.0 log reduction at 14 days from the previous value measured and no increase at 28 days from the previous measured value. See Table 1. For yeast and fungi, the USP requirement is for there to be no increase from the time of inoculation to 7, 14 and 28 days.

EP requirements are more stringent. EP 5th Edition 5.6 (5.1.3) requirements for parenteral and ophthalmic preparations has two components: Category A and Category B. Category A (EP-A) requires, for bacteria, at least 2.0 log reduction from the initial calculated count at 6 hours after inoculation, at least 3.0 log reduction at 24 hours from the previous measured value, and no recovery at 28 days. Category B (EP-B) requires, for bacteria, at least 1.0 log reduction at 24 hours from the initial calculated count, at least 3.0 log reduction at 7 days from the previous value measured and not more than 0.5 log increase at 28 days from the previous value measured (i.e., no increase). See Table 1. For yeast and fungi, Category A requires at least 2.0 log reduction at 7 days and no increase from the previous value measured at 28 days, and Category B requires at least 1.0 log reduction at 14 days and no increase from the previous value measured at 28 days.

Plates containing <300 CFU for bacteria or <100 CFU for yeast or mold were used during enumeration. For single challenge studies, arithmetic average count of all surviving micro-organisms in triplicate and on duplicate plates (6 values per time point) plus their diluted samples were measured and normalized as CFU/ml. The results are expressed as mean $\log_{10}$ CFU/ml reduction (compared to time 0). In this case, the count of surviving micro-organisms is evaluated at time 0 as the baseline and compared to incubation time of 6 hours, 24 hours, 7 days, 14 days and 28 days.

The preservatives tested showed no obvious impact on Prev(e)nar 13 stability except for the parabens (methylparaben and propylparaben), which showed a decreased in Prev(e)nar 13 bound antigenicity. Further, phenol, meta-cresol, methyl- and propylparabens interfered with the Modified Lowry protein assay (protein concentration of the vaccine is determined by the commercial available Modified Lowry protein assay).

Preservative effectiveness test (PET) results showed that all of the tested preservatives met the USP requirements but not the EP criteria (EP-A or EP-B). See Table 2. 2-PE was the only candidate preservative which was known to be safe at higher dosages. Therefore, further tests on preservative effectiveness, with higher doses of 2-PE, were pursued.

TABLE 2

The effectiveness of potential preservatives in meeting USP and EP* vaccine safety requirements after a single challenge of micro-organisms

| 0.5 mL dose | Challenge Organisms | | | | |
|---|---|---|---|---|---|
| | Bacteria | | | Yeast | Fungi |
| Preservative | *S aureus* | *E. coli* | *P. aeruginosa* | *C. albicans* | *A. niger* |
| 2-Phenoxy ethanol 5.0 mg/mL | | | | | |
| USP | Meets | Meets | Meets | Meets | Meets |
| EP | Fails | Fails | Fails | Fails | Fails |

TABLE 2-continued

The effectiveness of potential preservatives in meeting USP and EP* vaccine safety requirements after a single challenge of micro-organisms

| 0.5 mL dose | Challenge Organisms | | | | |
|---|---|---|---|---|---|
| | Bacteria | | | Yeast | Fungi |
| Preservative | *S aureus* | *E. coli* | *P. aeruginosa* | *C. albicans* | *A. niger* |
| 0.3% m cresol | | | | | |
| USP | Meets | Meets | Meets | Meets | Meets |
| EP | Fails | Fails | Fails | Meets | Meets |
| 0.18% methyl parabens and 0.02% propyl parabens | | | | | |
| USP | Meets | Meets | Meets | Meets | Meets |
| EP | Fails | Fails | Fails | Meets | Meets |
| 0.25% phenol | | | | | |
| USP | Meets | Meets | Meets | Meets | Meets |
| EP | Fails | Fails | Fails | Meets | Meets |

*EP-B

Example 2

Preservative Effectiveness Test by Single Challenge Method: 2-PE and Thimerosal Thimerosal at 0.01% concentration is commonly used in major vaccines licensed in the U.S. The effectiveness of Thimerosal as a preservative was tested using the same single-challenge method described above in Example 1. Prev(e)nar 13 vaccine formulation containing Thimerosal at 0.01% (equivalent to 25 μg mercury per 0.5 mL dose) did not meet the European acceptance criteria EP-A or EP-B established by preservative anti-microbial effectiveness method of EP. It however, did pass acceptance limits established by the U.S. or Japanese Pharmacopoeia, since the acceptance limits established by these compendial methods are less stringent compared to that established in EP. See FIG. 1.

Thimerosal at 0.02% (containing 50 μg mercury per dose), which is equivalent to twice the recommended concentration of Thimerosal in some of the U.S. licensed vaccines, or at 0.04% (containing 100 μg mercury per dose), which is equivalent to four times the recommended concentration of Thimerosal in some of the U.S. licensed vaccines, met the EP acceptance criteria B, but not the more stringent A acceptance criteria (with a single challenge of micro-organisms). See FIG. 1.

2-PE was more effective as a preservative than Thimerosal. While 2-PE at 2.5 mg/dose failed both EP acceptance criteria A and B, 2-PE at concentrations of 3.5 to 5.5 mg/dose met EP acceptance criteria B. At concentrations above 6.0 mg/dose, 2-PE met both EP-A and EP-B anti-microbial effectiveness acceptance criteria (FIG. 2).

Example 3

Single Challenge Method with 2-PE and Thimerosal: Change in Contaminant Level Absence of preservatives in the Prev(e)nar 13 vaccine formulation resulted in a slow growth of *P. aeruginosa*, no change to *C. albicans* levels and *A. niger* and slow reduction in colony forming units of *S. aureus* over a 28 days challenged period at 20-25° C. (FIG. 3).

Figure 4:
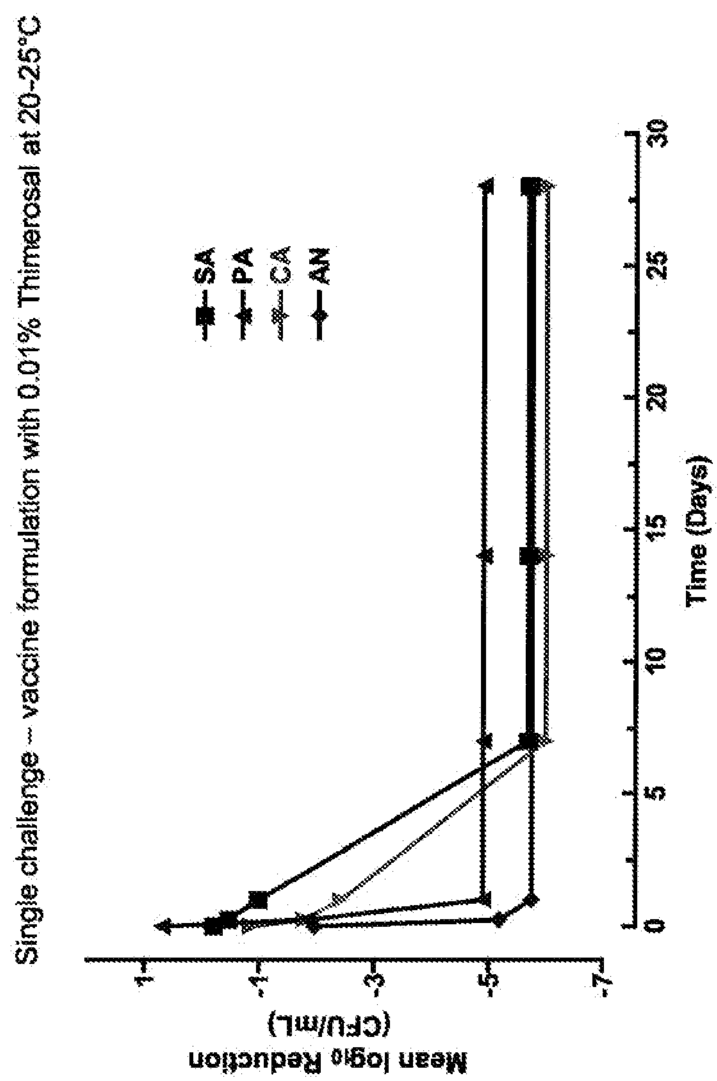
FIG. 4—Time course of micro-organism colony count reduction in Prev(e)nar 13 vaccine formulation with 0.01% Thimerosal at 20-25° C. after a single challenge of micro-organisms (expressed as mean $\log_{10}$ change compared to time of challenge at t=0, 6 hours, 24 hours, 7 days, 14 days and 28 days).
Figure 5:
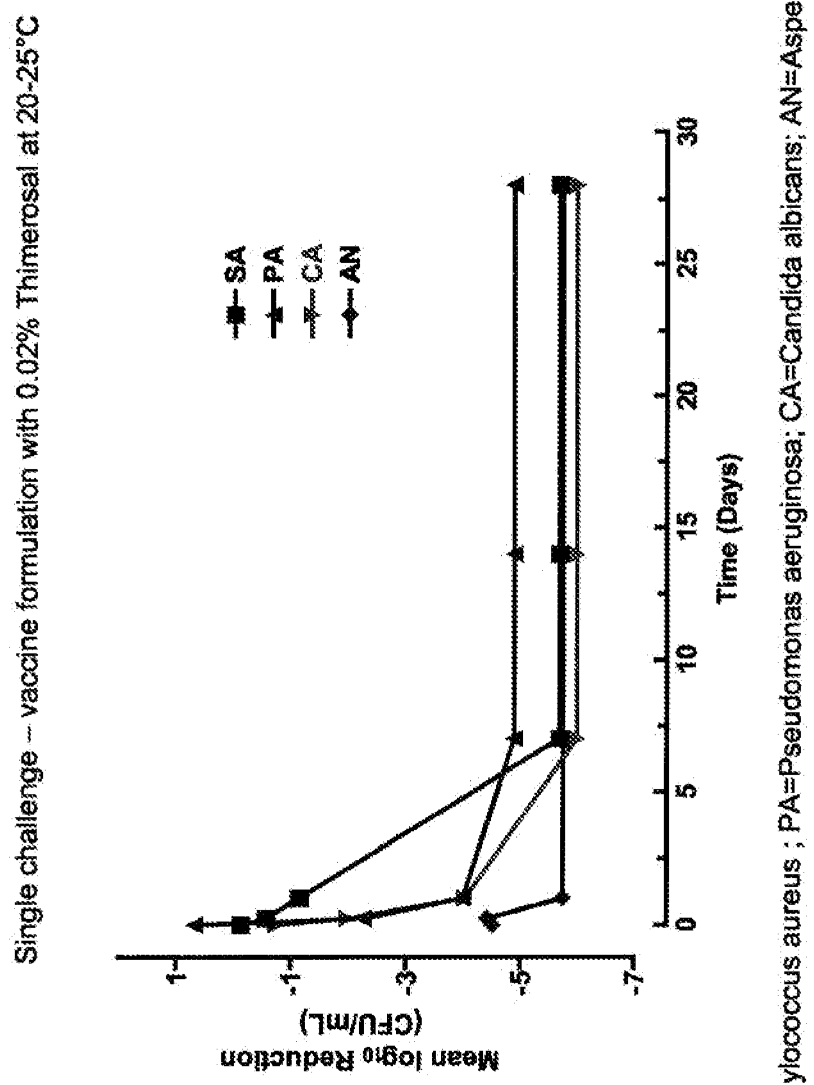
FIG. 5—Time course of micro-organism colony count reduction in Prev(e)nar 13 vaccine formulation with 0.02% Thimerosal at 20-25° C. after a single challenge of micro-organisms (expressed as mean $\log_{10}$ change compared to time of challenge at t=0, 6 hours, 24 hours, 7 days, 14 days and 28 days).
Figure 6:
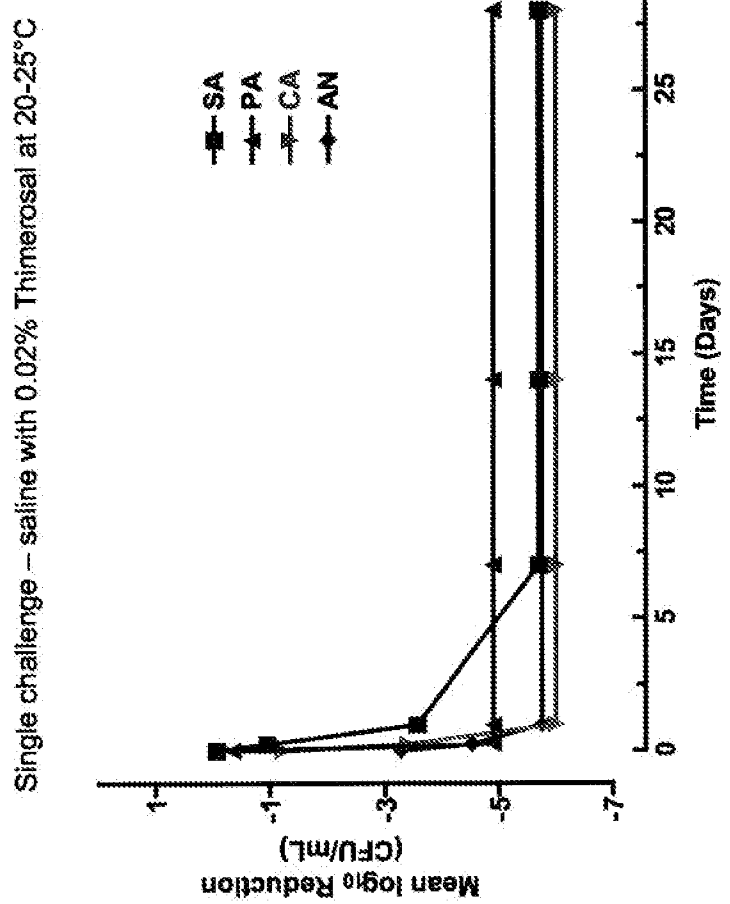
FIG. 6—Time course of micro-organism colony count reduction in saline with 0.02% Thimerosal at 20-25° C. after a single challenge of micro-organisms (expressed as mean $\log_{10}$ change compared to time of challenge at t=0, 6 hours, 24 hours, 7 days, 14 days and 28 days).

The presence of 0.01% Thimerosal (containing 25 μg mercury per dose) reduced the contamination levels of all four inoculated micro-organisms. However, the inhibition of *S. aureus* and *C. albicans* was weaker than the inhibition of *P. aeruginosa* and *A. niger* (FIG. 4). A dose response relationship on the rate of anti-microbial effect of Thimerosal in Prev(e)nar 13 vaccine formulations was seen, especially against *C. albicans*, with the reduction of contamination levels being more pronounced with 0.02% Thimerosal (FIG. 5). Absence of Prev(e)nar 13 in a 0.02% Thimerosal-containing saline formulation slightly improved the growth inhibitory effectiveness of Thimerosal against *S. aureus* and *C. albicans* (FIG. 6).

Figure 7:
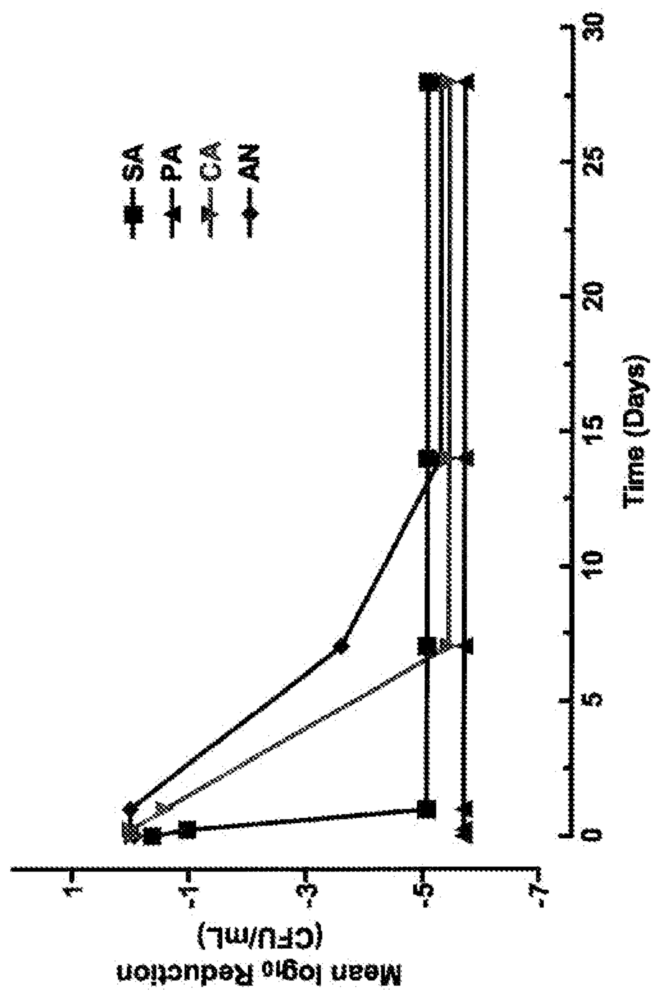
FIG. 7—Time course of micro-organism colony count reduction in Prev(e)nar 13 vaccine formulation with 5 mg/0.5 mL 2-phenoxyethanol at 20-25° C. after a single challenge of micro-organisms (expressed as mean $\log_{10}$ change compared to time of challenge at t=0, 6 hours, 24 hours, 7 days, 14 days and 28 days).

2-PE was more effective as a preservative than Thimerosal. For example, in contrast to the slow decline of *S. aureus* with Thimerosal, the anti-microbial efficacy of 5.0 mg/dose 2-PE resulted in reduction of *S. aureus* to baseline in 24 hrs after inoculation (FIG. 7). Although 2-PE was less effective than Thimerosal as a preservative against *A. niger* (FIG. 7), and the rate of decline of *A. niger* contamination was slower compared to Thimerosal (FIGS. 4 and 5), the superior effectiveness of 2-PE with regard to the other strains allowed it to meet the preservative acceptance criteria EP-B at a concentration of 3.5 and 5 mg/dose (FIG. 2), while 0.01% Thimerosal did not (FIG. 1).

Figure 14:
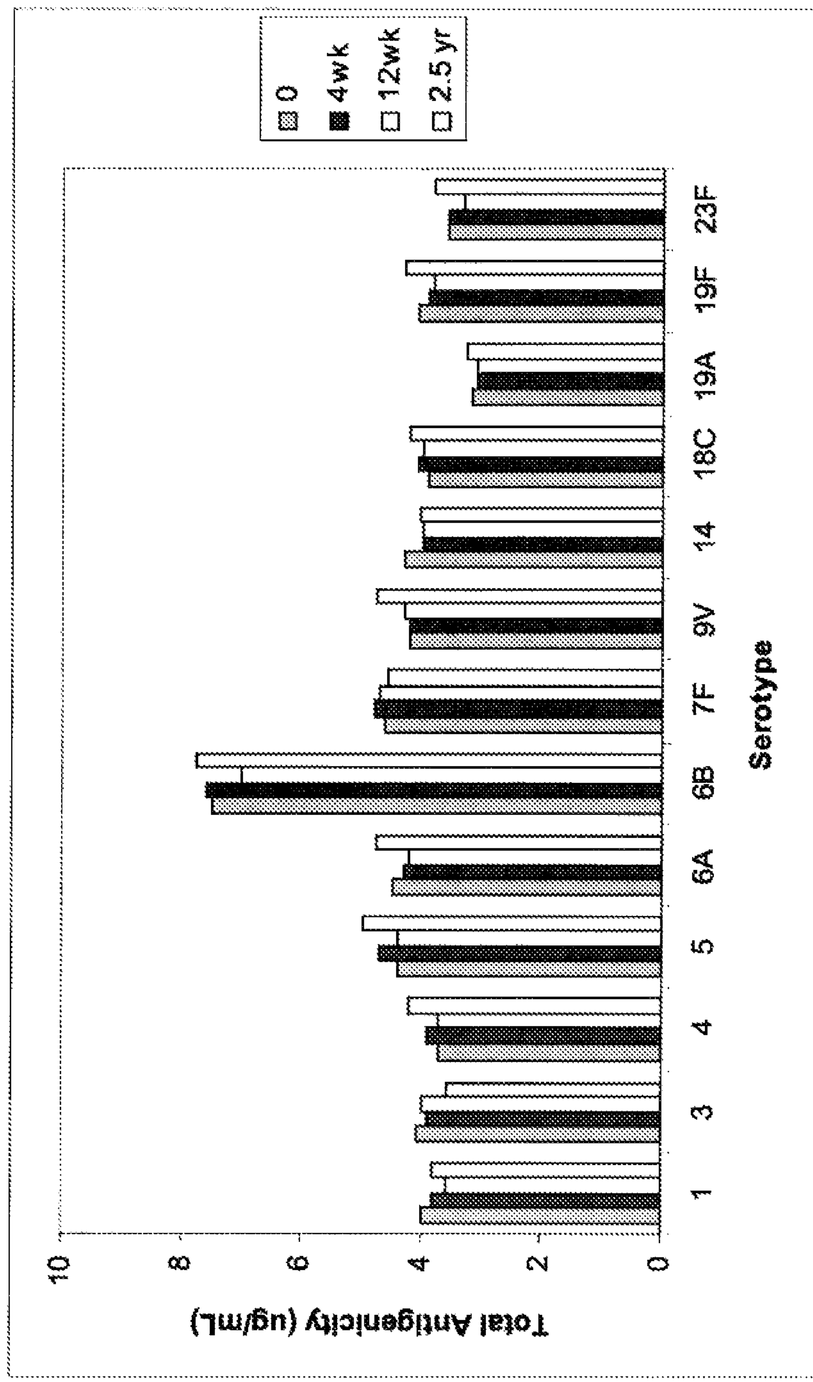
FIG. 14—Long term stability of antigenicity of *Streptococcus pneumoniae* polysaccharide preparations from each serotype in Prev(e)nar 13 formulated with 5 mg 2-PE.
Figure 15:
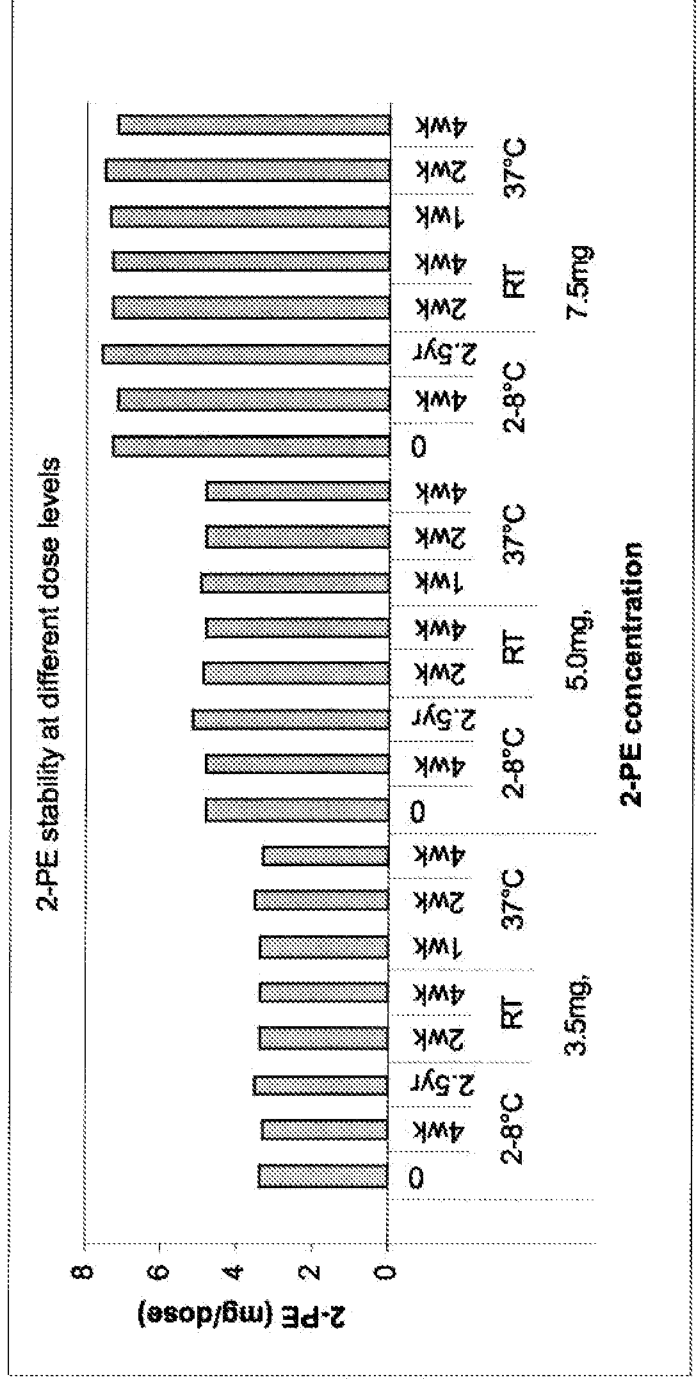
FIG. 15—Long term stability of 2-PE in Prev(e)nar 13 vaccine formulation.

The preservative effectiveness of 2-PE at 3.5 to 5.0 mg/dose remained persistent when formulations were stored at 37° C. for a month or at 2-8° C. for two and a half years (FIG. 2). The concentration of 2-PE in the formulation was similarly stable (FIG. 15). The immunological activity (total antigenicity) of each of the 13 serotypes present in the Prev(e)nar 13 formulation was also stable under these storage conditions (FIG. 14).

Total antigenicity was derived from both bound and unbound polysaccharides present in the vaccine for each serotype. Type-specific antigenicities were determined by using type-specific anti-sera. Prior to the assay, the 13-valent vaccine formulated with aluminum phosphate was first solubilized. The solution was then neutralized to avoid alkaline-induced degradation. Using a Nephelometer, the assay measured the rate of change of light scattering intensity derived from the antibody-antigen complex formation. Antigenicities of test samples were determined by linear regression using standard curves measured immediately before or after analysis of samples.

In order to assure of Thimerosal content of the Prev(e)nar 13 vaccine and saline formulations, the concentration of mercury was determined in some of the formulations by the method of Cold Vapor Atomic Absorption Spectrometry (CVAAS). The measured concentration of mercury was very close to its predicted values, suggesting that Thimerosal concentration in these formulations were on target and not underestimated. The measured concentration of 2-PE was also very close to its predicted value and did not change upon storage of Prev(e)nar 13 formulations over time at either 2-8° C. or 37° C. 2-PE concentration was measured with a Reversed-Phase HPLC assay. Samples were vortexed and diluted 1:10 into 5 mM Succinate buffer in saline, centrifuged and diluted again 1:10 into 5 mM succinate buffer in saline. Final dilution of the Test Sample was 1:100. The assay utilized the Agilent Eclipse XDB-C18 HPLC column and a linear gradient of water and acetonitrile containing trifluoroacetic acid. 2-PE in 13vPnC Multi-Dose Vaccine samples was quantified against a 2-PE standard curve. See also, Sharma et al., *Biologicals* 36(1): 61-63 (2008).

Example 4

Preservative Effectiveness Test by Multi-Challenge Method: Thimerosal

To assess the appropriateness of WHO multi-dose Open Vial Policy of vaccines in multiple immunization sessions for up to maximum of four weeks, experimental design provided by WHO was implemented. In this study, the effectiveness of Thimerosal was evaluated at the concentration that is present in the majority of U.S. licensed vaccines (0.01%), as well as at a higher concentration of 0.02%. To represent the worst reasonable case of contamination that may occur in practice during the repeated use of a multi-dose presentation, and to test WHO requirements, Prev(e)nar 13 vaccine formulations with 0.01 or 0.02% Thimerosal or with 5.0 mg/dose of 2-PE were deliberately exposed to multiple contamination events using WHO recommended bacterial strains, *P. aeruginosa, S. aureus, E. coli* and *B. subtilis*. Formulations were spiked with $5\times10^3$ CFU/ml of each organism at times 0, 6 hours, 24 hours, 7 days and 14 days after initial challenge and stored either at 2-8° C. or at 22-24° C. to mimic the potential storage conditions in practice. Saline formulation containing 0.02% Thimerosal was also used as a control to evaluate the potential impact of Prev(e)nar 13 on the antimicrobial efficacy of Thimerosal in the formulation.

Figure 8:
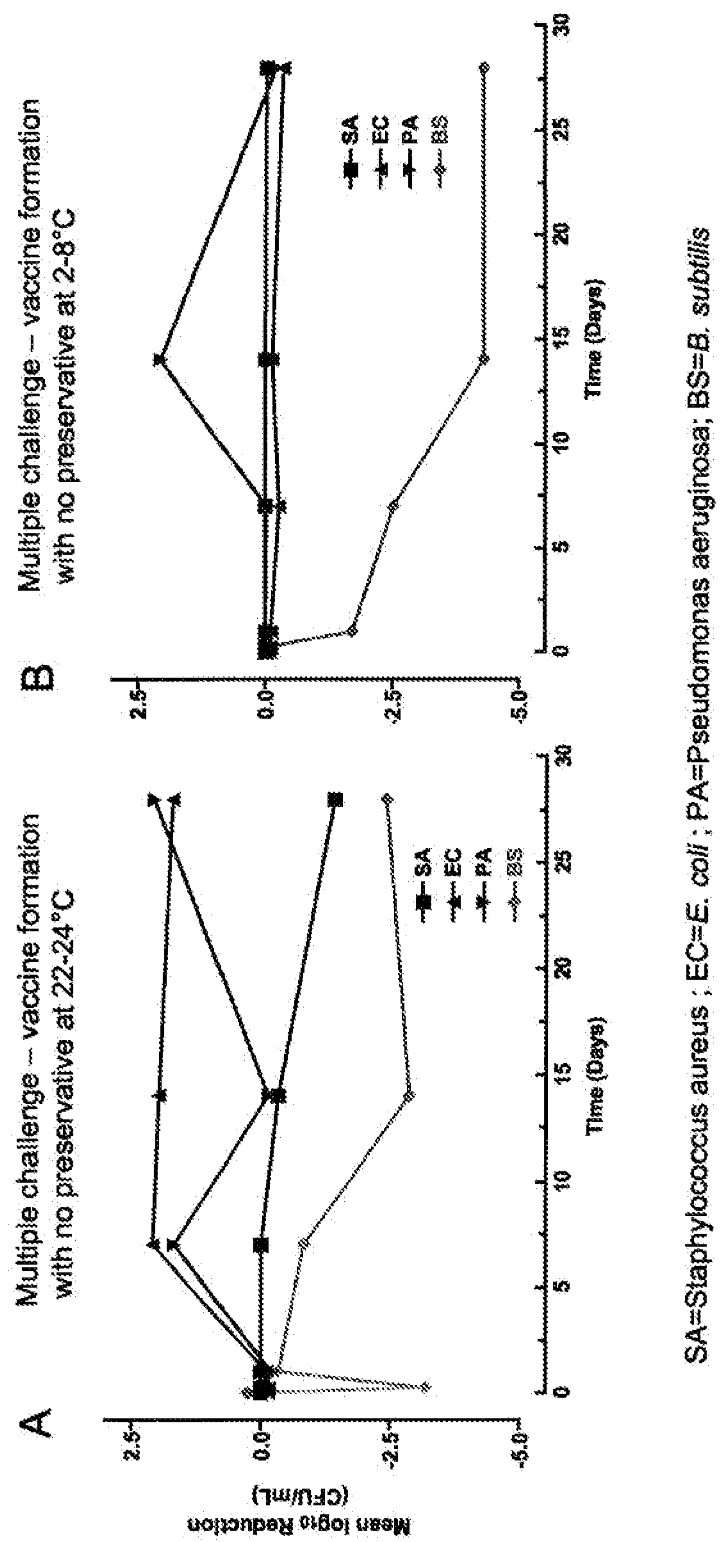
FIG. 8—Time course of micro-organism colony count reduction in Prev(e)nar 13 vaccine formulation with no preservative at (A) 22-24° C. or at (B) 2-8° C., after multiple challenges of micro-organisms at t=0, 6 hours, 24 hours, 7 days and 14 days (expressed as mean $\log_{10}$ change compared to time of challenge at t=0, 6 hours, 24 hours, 7 days, 14 days and 28 days).

Upon multiple deliberate contaminations of Prev(e)nar 13 vaccine formulation in the absence of a preservative, the level of *P. aeruginosa* and *E. coli* organisms increased over the course of study, especially when stored at 22-24° C. (FIGS. 8A and 8B). The level of *S. aureus* in formulation stored at 22-24° C. slowly declined, similar to that observed during the single challenge study (FIG. 8A compare to FIG. 3). The viability of *B. subtilis* declined even more noticeably (FIGS. 8A and 8B). These results suggest that *B. subtilis* is not a robust organism in this formulation to be used as a model for such challenge studies in preservative effectiveness test, despite it's recommendation by the WHO.

In the Prev(e)nar 13 vaccine formulation, the antibacterial effectiveness of 0.01% Thimerosal was highest on *B. subtilis* followed by *P. aeruginosa*. However, the reduction of *S. aureus* and *E. coli* was slow, particularly when the formulations were stored at 2-8° C. (FIGS. 9A and 9B).

As shown in the non-linear regression analysis of decay in the viability of *S. aureus* is summarized in FIG. 12, the rate of decay of *S. aureus* was substantially slower (−5.98 $\log_{10}$ decay per day, with 50% decay in 30.28 days) when formulation was stored at 2-8° C. compared to that stored at 22-24° C. (−1.39 $\log_{10}$ decay per day, with 50% decay in 6.2 days) (FIG. 12). These results show that 0.01% Thimerosal in a Prev(e)nar 13 vaccine formulation, being contaminated in the field during multi-dose delivery, and further stored at refrigerated temperature, will not be effective in reducing bacterial contamination.

Figure 9:
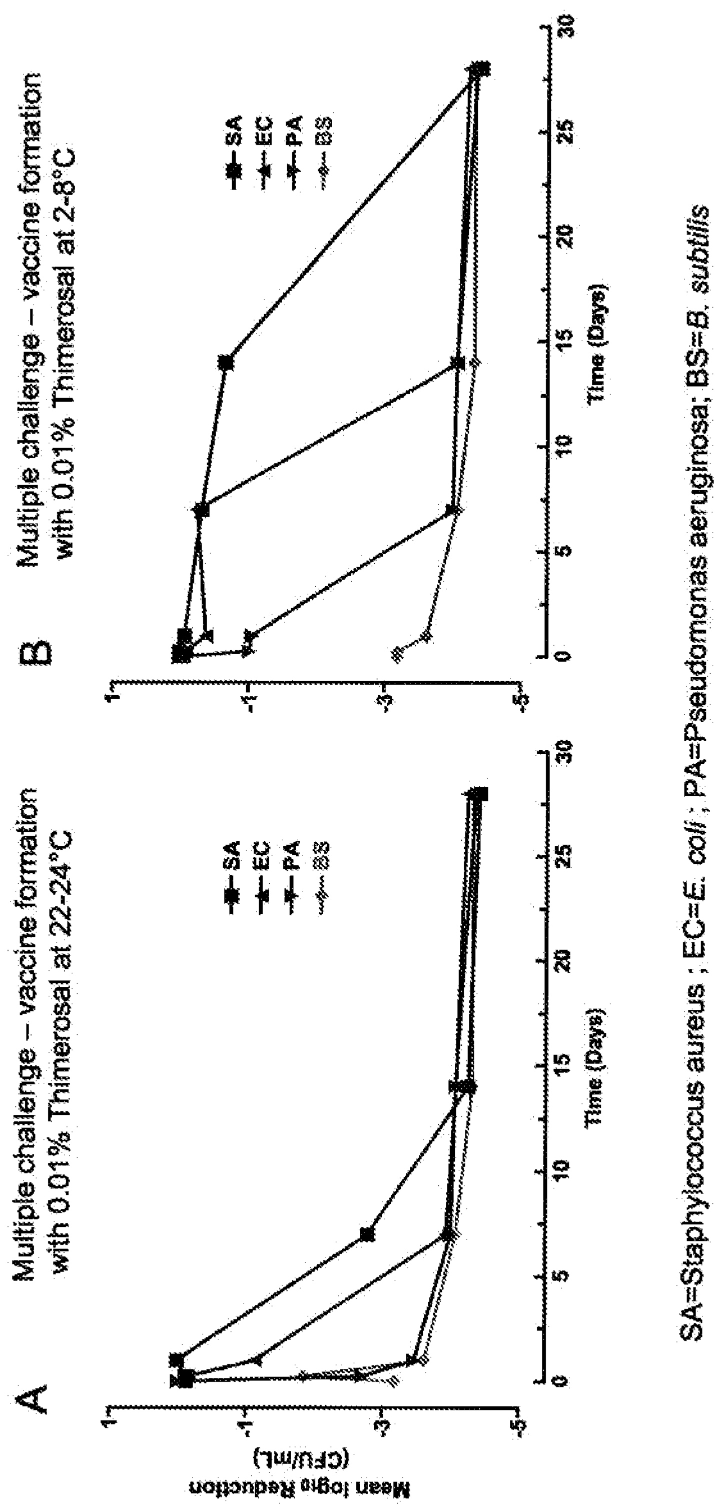
FIG. 9—Time course of micro-organism colony count reduction in Prev(e)nar 13 vaccine formulation with 0.01% Thimerosal at (A) 22-24° C. or at (B) 2-8° C., after multiple challenges of micro-organisms at t=0, 6 hours, 24 hours, 7 days and 14 days, (expressed as mean $\log_{10}$ change compared to time of challenge at t=0, 6 hours, 24 hours, 7 days, 14 days and 28 days).
Figure 10:
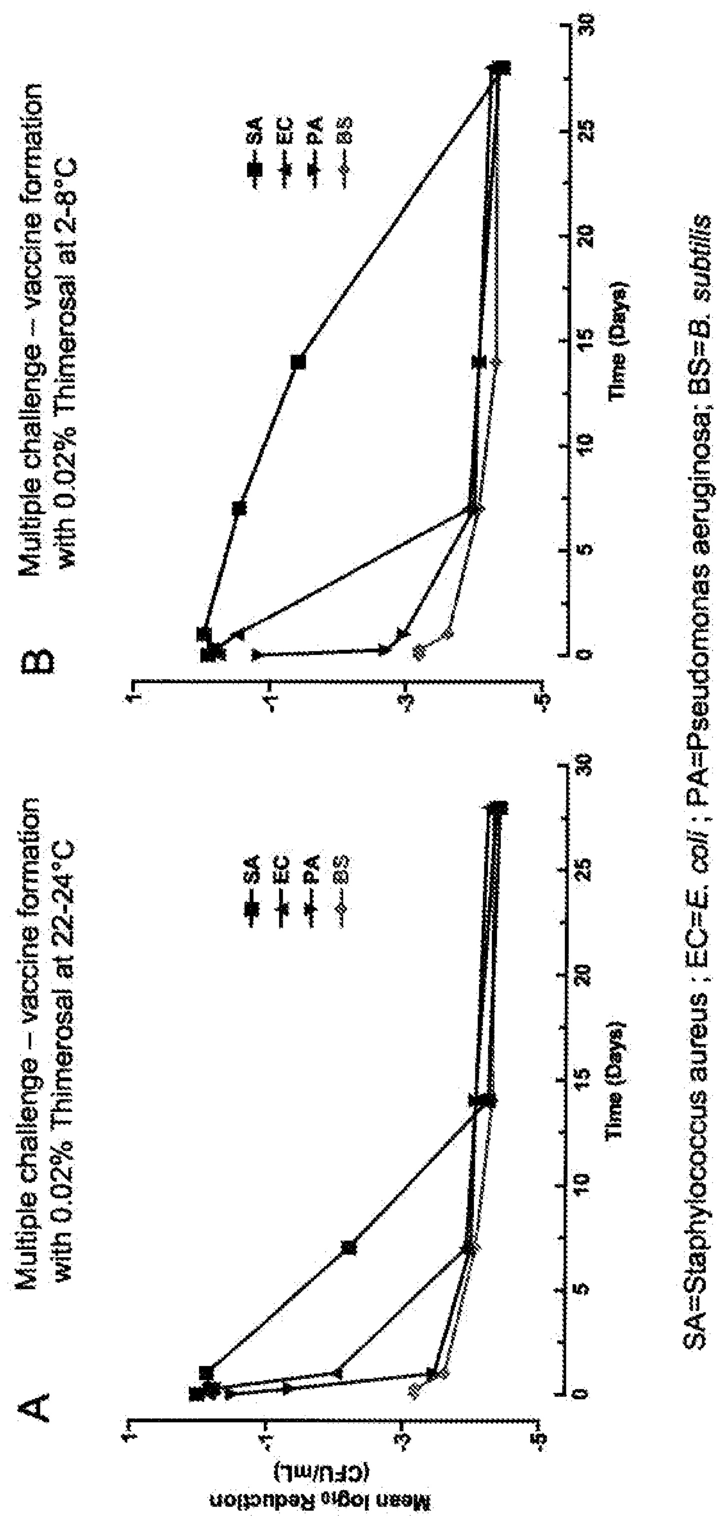
FIG. 10—Time course of micro-organism colony count reduction in Prev(e)nar 13 vaccine formulation with 0.02% Thimerosal at (A) 22-24° C. or at (B) 2-8° C. after multiple challenges of micro-organisms at t=0, 6 hours, 24 hours, 7 days and 14 days (expressed as mean $\log_{10}$ change compared to time of challenge at t=0, 6 hours, 24 hours, 7 days, 14 days and 28 days).

The effectiveness of Thimerosal was both concentration and temperature dependent (FIGS. 9 and 10). Thimerosal was a more effective preservative at the higher concentration of 0.02%. It was also a more effective preservative at the higher storage temperature of 22-24° C. However, as discussed above, even with 0.02% concentration and 22-24° C. storage, Thimerosal did not meet the EP requirements of either EP-A or EP-B when such criteria were applied during the multi-challenge studies (FIG. 1).

Figure 11:
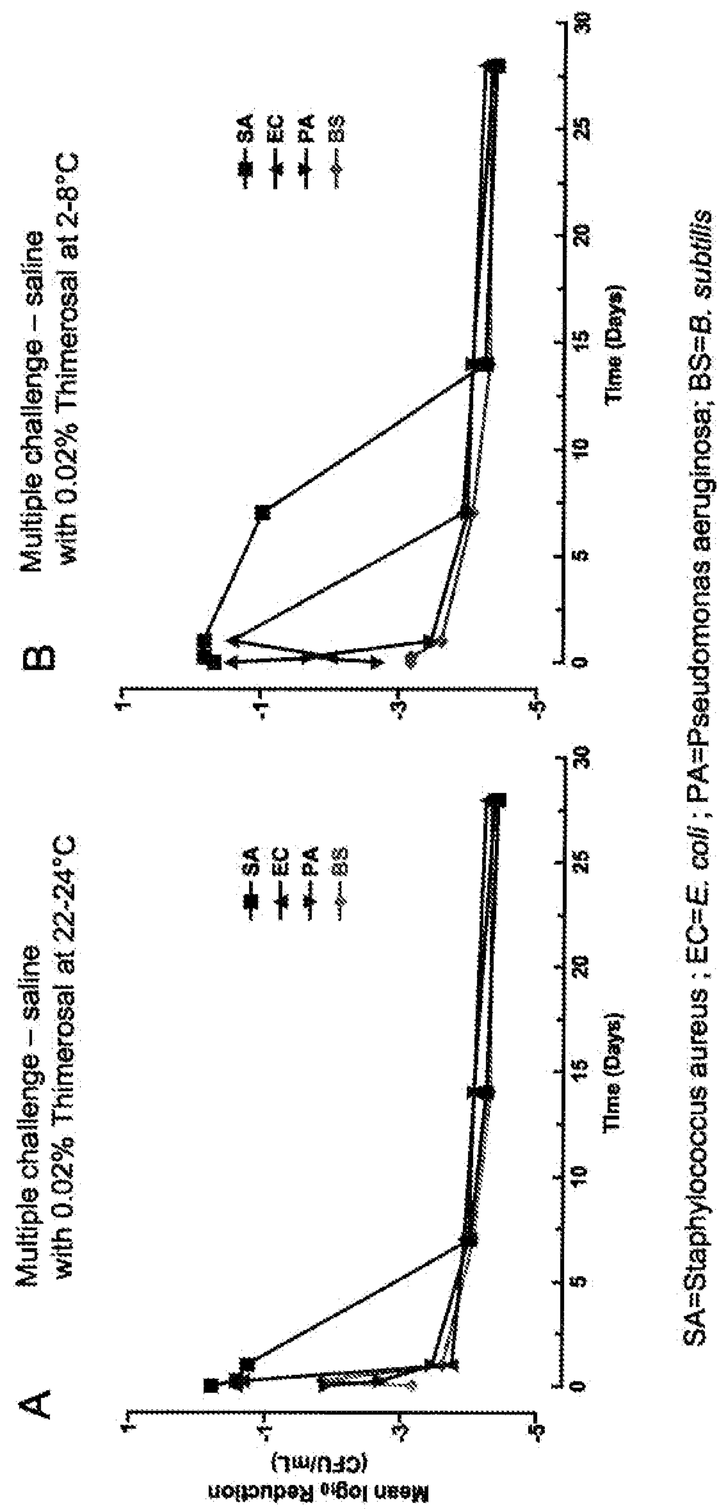
FIG. 11—Time course of micro-organism colony count reduction in saline with 0.02% Thimerosal at (A) 22-24° C. or at (B) 2-8° C. after multiple challenges of micro-organisms at t=0, 6 hours, 24 hours, 7 days and 14 days (expressed as mean $\log_{10}$ change compared to time of challenge at t=0, 6 hours, 24 hours, 7 days, 14 days and 28 days).

To study whether or not the vaccine itself affects the preservative action of Thimerosal, the effectiveness of 0.02% Thimerosal with multiple challenges was compared between saline and the Prev(e)nar 13 vaccine formulation. In the presence of 0.02% Thimerosal, the rate of decay of both *S. aureus* and *E. coli* was more pronounced in saline formulation than in the vaccine formulation (FIG. 11 compare to FIG. 10 and FIG. 12), demonstrating that the presence of the vaccine, to some extent, inhibited the effectiveness of Thimerosal as a preservative. Nevertheless, even in a saline control formulation that did not contain the vaccine, 0.02% Thimerosal still did not meet the acceptance criteria of EP-A or EP-B when multiply challenged (FIG. 1).

Example 5

Preservative Effectiveness Test by Multi-Challenge Method: 2-PE

In contrast to the lack of effectiveness of Thimerosal as a preservative, especially when multiply inoculated or stored at 2-8° C., Prev(e)nar 13 vaccine formulation containing 5 mg/dose of 2-PE as the preservative results in a stronger inactivation of *S. aureus* viability, regardless of challenge method (i.e., single or multiple) or storage temperature (FIG. 12).

In fact, with the multi-challenge method, regardless of the storage temperature, and with all the organisms tested (*P. aeruginosa, S. aureus, E. coli* and *B. subtilis*), 5 mg/dose 2-PE was superior as a preservative over 0.01% Thimerosal. In a non-linear regression analysis of *S. aureus* decay in various challenge studies, the vaccine formulations with 2-PE had a faster rate of microbial contaminant decay than those with Thimerosal both in terms of 50% decay and average slope of decay ($\log_{10}$ decay/day). See FIG. 12. Further, 5 mg/dose 2-PE met the EP-B criteria under multiple challenge, while no version of Thimerosal was able to do so under the same conditions (FIG. 13).

Thimerosal is not an effective preservative in protecting Prev(e)nar 13 in multi-dose formulation against potential contamination that may be introduced during dispensation. This is even more evident when contamination is introduced multiple times during dosing subjects in multi-dose formulations. Thimerosal has a slow rate of inactivation, particularly against *S. aureus* and *E. coli*, with a lagging immediate effect to clear the potential contaminating organisms when general practitioners might withdraw vaccines from multi-dose vials under poor hygienic conditions. However, 2-PE at 3.5 to 5 mg/dose is stable with a much higher rate of antimicrobial effectiveness compared to Thimerosal and therefore will protect the product from inadvertent contamination while dosing subjects.

Example 6

Immune Response Elicited by Immunization of Prevenar 13 with or without 2-Phenoxy Ethanol as a Preservative in Nonhuman Primates The ability of Prevenar 13 and Prevenar 13 containing 2-phenoxy ethanol to induce immune response is evaluated in cynomolgus macaques.

Two immunization groups of 10 macaques for a total of 20 cynomolgus macaques are used for the study as detailed at Table 3.

TABLE 3

| Group | Macaques/ group | Vaccine | Final volume | Delivery |
|---|---|---|---|---|
| 1 | 10 | 13vPnC | 0.5 mL | IM |
| 2 | 10 | 13vPnC + 5 mg 2PE | 0.5 mL | IM |

Prescreened animals are randomized into groups based on their body weights and baseline titers.

Macaques are given the clinical dose of 13vPnC containing 0 or 5 mg of 2-phenoxyethanol as preservative. The vaccine is given intramuscularly at a single site in the quadriceps muscle of each monkey. The final volume delivered is 0.5 mL.

All macaques receive three doses and are vaccinated at week 2, 4 and 8.

Bleed Schedule: Peripheral blood is sampled at week 0, 6, 8, 10, 12 and 16 to monitor the induction of immune responses to the vaccines.

Immune response elicited by vaccination is monitored by performing the below assays on serum collected during the study:

- In vitro binding and functional antibodies:
  - Serotype-specific IgG by ELISA (see e.g. Fernsten P, et al., Hum Vaccin. 2011 Jan. 1; 7:75-84)
  - Serotype-specific opsonophagocytosis assay (OPA) (see e.g. Fernsten P, et al., Hum Vaccin. 2011 Jan. 1; 7:75-84)
- In vivo protection in the infant rat challenge model (see e.g. Fernsten P, et al., Hum Vaccin. 2011 Jan. 1; 7:75-84):
  - Pooled macaque sera is evaluated for serotype-specific protection.

The invention claimed is:

1. A multivalent immunogenic composition comprising a polysaccharide-protein conjugates consisting of pneumococcal capsular polysaccharides from *Streptococcus pneumoniae* serotypes 1, 3, 4, 5, 6A, 6B, 7F, 9V, 14, 18C, 19A, 19F and 23F, individually conjugated to $CRM_{197}$, and further comprising not less than 7 mg/mL of2-phenoxyethanol (2-PE).

2. The multivalent immunogenic composition of claim 1, wherein said composition comprises 2-PE at a concentration of between 7 mg/mL and 15 mg/mL.

3. The multivalent immunogenic composition of claim 2, wherein said composition comprises 2-PE at a concentration of about 10 mg/mL.

4. The multivalent immunogenic composition of claim 1, wherein said composition comprises not less than 10 mg/mL of 2-PE.

5. The multivalent immunogenic composition of claim 1, wherein said composition comprises not less than 15 mg/mL of 2-PE.

6. The multivalent immunogenic composition of claim 1, wherein said composition further comprises an adjuvant, and wherein said adjuvant is aluminum phosphate.

7. The multivalent immunogenic composition of claim 1, wherein the antigenicity of the immunogenic composition is stable for not less than 1 year, 1.5 years, 2 years or 2.5 years.

8. The multivalent immunogenic composition of claim 1, wherein, following inoculation of the composition with one or more micro-organisms, the concentration of said micro-organisms is reduced over time.

9. The multivalent immunogenic composition of claim 8, wherein, following inoculation with one or more bacteria strains, the composition presents at least 1.0 log reduction from the initial micro-organism count at 24 hours, at least 3.0 log reduction at 7 days from the previous value measured and not more than 0.5 log increase at 28 days from the previous value measured.

10. The multivalent immunogenic composition of claim 8, wherein, following inoculation with one or more bacteria strains, the composition presents at least 2.0 log reduction from the initial calculated count at 6 hours after inoculation, at least 3.0 log reduction at 24 hours from the previous value measured and no recovery at 28 days.

11. The multivalent immunogenic composition of claim 8, wherein the one or more micro-organisms are selected from the group consisting of *P. aeruginosa, S. aureus, E. coli* and *B. subtilis.*

12. The multivalent immunogenic composition of claim 8, wherein the composition is inoculated multiple times.

13. The multivalent immunogenic composition of claim 12, wherein a second inoculation occurs at 6 hours following an initial inoculation, a third inoculation occurs at 24 hours following the initial inoculation, a fourth inoculation occurs at 7 days following the initial inoculation and a fifth inoculation occurs at 14 days following the initial inoculation.

14. The multivalent immunogenic composition of claim 1, wherein said composition further comprises one or more of a buffer, a cryoprotectant, a salt, a divalent cation, a non-ionic detergent, and an inhibitor of free radical oxidation.

15. A multivalent immunogenic composition formulation of pneumococcal capsular polysaccharides from serotypes 1, 3, 4, 5, 6A, 6B, 7F, 9V, 14, 18C, 19A, 19F and 23F, individually conjugated to $CRM_{197}$, wherein the multivalent immunogenic composition is formulated in a sterile liquid to comprise: about 4.4 μg/mL of each polysaccharide, except for 6B at about 8.8 μg/mL; about 58 μg/mL $CRM_{197}$ carrier protein; about 0.25 mg/mL of elemental aluminum in the form of aluminum phosphate; about 0.85% sodium chloride; about 0.02% polysorbate 80; about 5 mM sodium succinate buffer at a pH of 5.8; and about 10 mg/mL of 2-phenoxyethanol.

16. A vial containing a multivalent immunogenic composition of claim 1.

17. The vial of claim 16, wherein said vial contains more than one dose of the immunogenic composition.

18. A pre-filled vaccine delivery device comprising a multivalent immunogenic composition of claim 1.

19. The pre-filled vaccine delivery device of claim 18, wherein said device comprises a syringe.

20. The pre-filled vaccine delivery device of claim 18, wherein said device comprises a dual or multiple chamber syringe or vials or combinations thereof.

21. The pre-filled vaccine delivery device of claim 18, wherein said multivalent immunogenic composition is formulated for intramuscular or subcutaneous injection.

22. A container comprising two doses or more of the multivalent immunogenic composition of claim 1, wherein each dose comprises 0.1 to 2 mL of the composition.

23. The multivalent immunogenic composition of claim 1, wherein said composition comprises 2-PE at a concentration of 4.0 mg/dose, wherein the dose is a 0.5 mL dose.

24. A multivalent immunogenic composition comprising pneumococcal capsular polysaccharides from serotypes 1, 3, 4, 5, 6A, 6B, 7F, 9V, 14, 18C, 19A, 19F and 23F, individually conjugated to $CRM_{197}$, wherein the multivalent immunogenic composition is formulated to comprise: about 4.4 μg/mL of each polysaccharide, except for 6B at about 8.8 μg/mL; from 20 to 100 μg/mL $CRM_{197}$; from 0.02 to 2 mg/mL of aluminum phosphate; from 0.5 to 21.25% sodium chloride; from 0.002 to 0.2% polysorbate 80; from 1 to 10 mM sodium succinate buffer at a pH of from 4 to 7; and between 7 mg/mL and 15 mg/mL of 2-phenoxyethanol.

* * * * *